United States Patent [19]

Tedders, Jr. et al.

[11] Patent Number: 5,484,504

[45] Date of Patent: Jan. 16, 1996

[54] DEVICE FOR ATTACHING EGGS OF PREDACEOUS INSECTS TO STRING AND A DELIVERY SYSTEM

[75] Inventors: Walker L. Tedders, Jr.; John L. Blythe, both of Perry, Ga.

[73] Assignee: The United States of America as represented by the Secretary of Agriculture, Washington, D.C.

[21] Appl. No.: 175,058

[22] Filed: Dec. 29, 1993

[51] Int. Cl.⁶ ........................................... B05B 7/14
[52] U.S. Cl. .................... 156/433; 156/578; 118/308; 118/309
[58] Field of Search ................................ 156/166, 433, 156/578, 556; 118/234, 408, 312, DIG. 21, DIG. 22, 308, 309; 427/174, 175, 180, 185; 242/172, 173, 170, 171, 176, 157.1, 158 R, 158.1, 158 B; 53/450; 47/56

[56] References Cited

U.S. PATENT DOCUMENTS

| | | | |
|---|---|---|---|
| 40,801 | 12/1863 | Beck | 427/180 |
| 2,338,722 | 2/1943 | Jackson | 242/176 |
| 2,539,267 | 1/1951 | Nikles | 242/158 R |
| 2,601,620 | 6/1952 | Marshall | 53/550 |
| 2,602,418 | 7/1952 | Paasche | 118/312 |
| 3,000,493 | 9/1961 | Hirst | 242/170 |
| 3,310,448 | 3/1967 | Tupper | 47/56 |
| 3,354,013 | 11/1967 | Terrell et al. | 427/185 |
| 3,456,386 | 7/1969 | Holden | 47/56 |
| 3,646,909 | 3/1972 | Cole et al. | 118/309 |
| 3,847,113 | 11/1974 | Andreev et al. | 118/40 |
| 4,260,108 | 4/1981 | Maedgen et al. | 239/171 |
| 4,966,329 | 10/1990 | Show | 239/650 |

FOREIGN PATENT DOCUMENTS

| | | |
|---|---|---|
| 2532730 | 2/1931 | Australia . |
| 231721 | 7/1910 | Germany . |

OTHER PUBLICATIONS

Entomophaga 31 (4), 1986, 397–400. Predation by Iridomyrmex Humilis on Eggs of Chrysoperla Carnea Released for Inundative Control of Illinoia Liriodendri Infesting Liriodendron Tulipifera. S. H. Dreistadt et al.
Trans. R. Ent. Soc. Lond. 127 (2), 1975, 115–140. The biology of Chrysopidae and Hemerobiidae (neuroptera), with reference to their usage as biocontrol agents: a review. T. R. New.

Primary Examiner—Michael W. Ball
Assistant Examiner—Richard Crispino
Attorney, Agent, or Firm—Gail E. Poulos; Howard Silverstein; John Fado

[57] ABSTRACT

Devices for loading beneficial insect eggs are disclosed which have a string supply, an egg receptacle, and a provision for applying glue. The devices provide an economical and alternative strategy for the delivery of beneficial insect eggs to agricultural commodities.

3 Claims, 24 Drawing Sheets

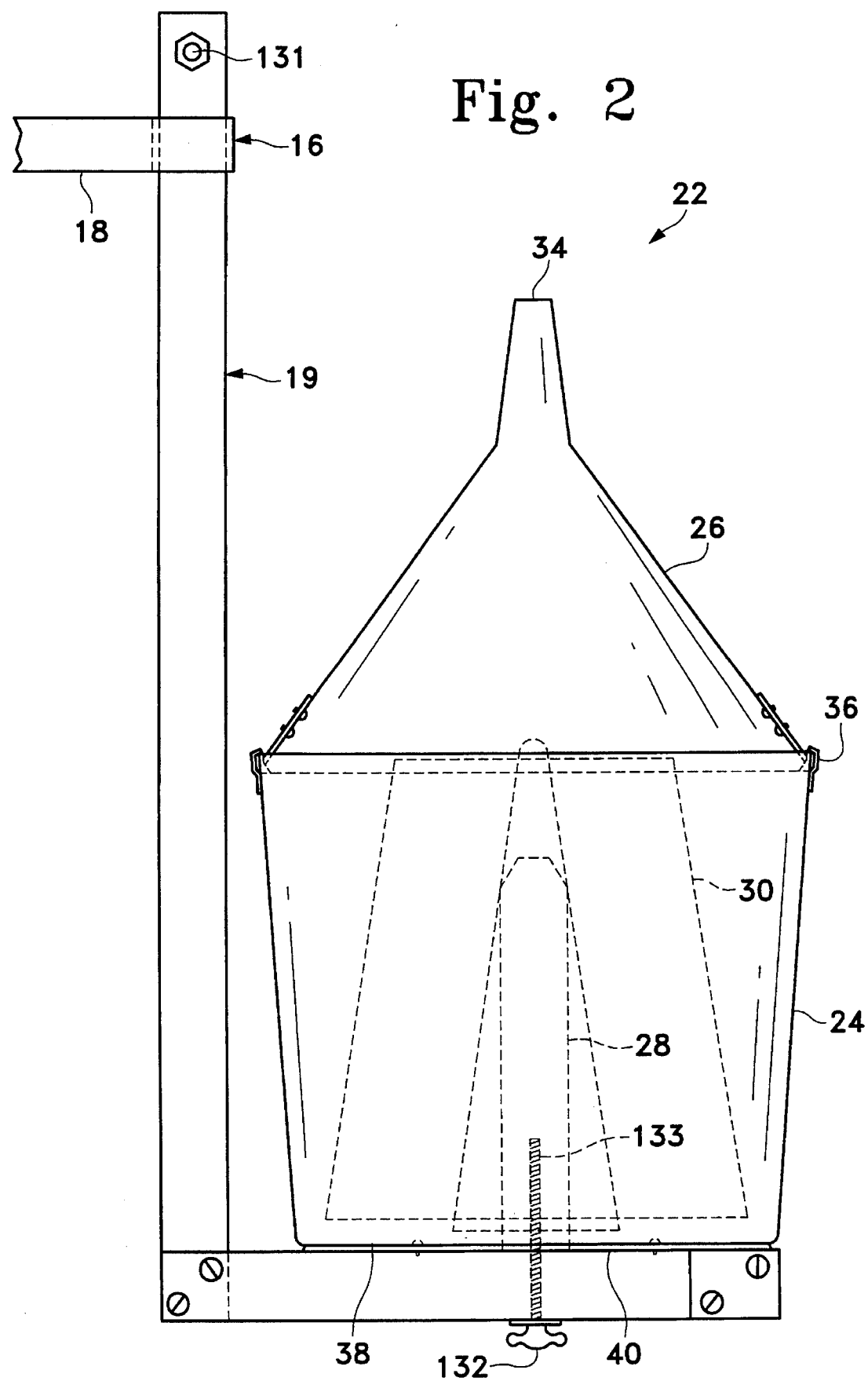

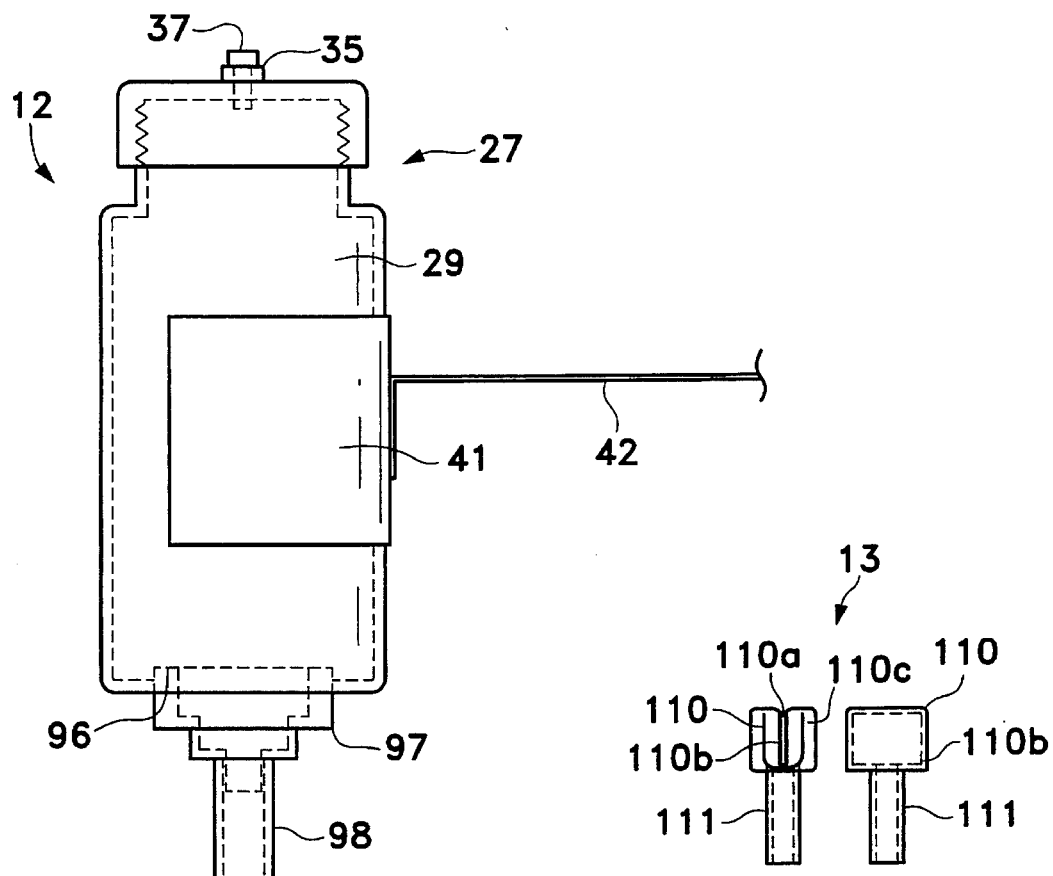
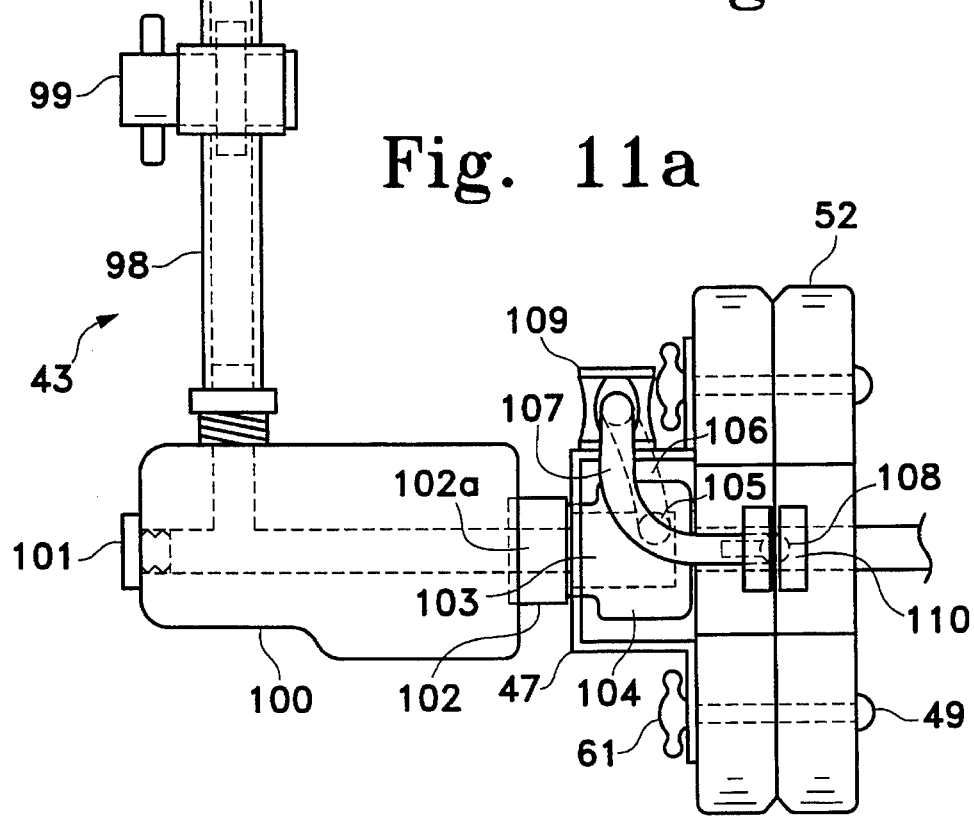
Fig. 11b
Fig. 11a

DEVICE FOR ATTACHING EGGS OF PREDACEOUS INSECTS TO STRING AND A DELIVERY SYSTEM

FIELD OF THE INVENTION

This invention relates to devices for attaching beneficial insect eggs to string. The eggs are directly applied to string which is then directly applied to plants as the string feeds from the device or when the string is cut into predetermined lengths to be manually placed on rows of plants. In an alternate embodiment, eggs are applied to string using a hand-cranked device which is suitable for small-scale plant growers and greenhouse operators. The string is cut from the device in predetermined lengths to be manually placed on individual plants.

BACKGROUND OF THE INVENTION

Chemical insecticides are used to control insects that damage agricultural commodities such as grapes, cotton, barley, citrus, pecans, Christmas trees, etc. However, recent concerns about insecticide residues on commodities, resistance of insects to chemical insecticides, hazardous exposure to pesticide applicators, environmental contamination, destruction of natural biocontrol agents, such as beneficial insects, and lack of newly developed insecticides have increased the need for alternative control methods. Furthermore, as pests become more resistant to pesticides, more frequent treatments are required which increases the human health hazard.

An alternative to chemical pesticides is the use of biocontrol agents such as beneficial or predaceous insects which eat harmful insects. To date, there is no practical or adequate way to deliver known quantities of predaceous insects to pest infested plants. Eggs are usually applied to plants by shaking them from a container onto the plant foliage. A large percent of the eggs fall to the ground and are quickly destroyed by ants and other predators. Larvae that emerge from the fallen eggs which escape predators are usually unable to find their way back up the plant and starve to death and the infesting insect on the plant continues to do damage. Some lacewing producers sell larvae from hatched eggs which are then shaken onto plants. However, this too is very inefficient since lacewings are cannibalistic, and when confined to a container consume each other. Furthermore, when larvae are shaken onto plants, like the unhatched eggs, most of the larvae fall to the ground and are destroyed by ants or starve to death. One prior art method (Dreistadt et al, Entomophaga, Volume 31(4), pp. 397–400, 1986), discloses the use paper strips with thin lines of rubber cement for attaching lacewing eggs for placement in trees. The paper tapes are prepared manually and attached to trees manually. The disclosed process takes several days since the rubber cement has to dry for several days prior to attachment of the eggs in order to eliminate toxic solvents. Upon hatching, larvae tend to become entangled by the tacky rubber cement and die. There are various types of prior art devices for attaching and delivering beneficial insect eggs to agricultural commodities. For example, U.S. Pat. No. 3,847,113 ('113) discloses a device which pastes insect eggs on a substratum. The '113 device is not designed for field use and requires several additional labor intensive acts. Eggs of a host insect are applied in a single layer to paper and excess eggs are vibrated or scraped off. The layer of host insect eggs on paper is then exposed to a parasitic wasp such as Trichogramma spp. in a separate cage where the eggs are parasitized by the Trichogramma. The excess eggs, which would have been vibrated or scraped off, would necessarily have to be manually recycled into egg loading 1 bin of '113. In order to apply eggs of other beneficial insects, such as lacewing eggs which are 25 times larger than the host egg used in '113, it would be necessary to use large amounts of filler in order to distribute only a few eggs onto the glued surface in order to prevent cannibalism once the eggs hatch. Furthermore, the device disclosed in '113 does not separate the paper with eggs into narrow strips which could be distributed over long distances but instead separates the paper into squares that are manually attached to plants. If long lengths of narrow paper were prepared, it would require manual preparation of the strips and some method of attachment to plants at frequent intervals. In transporting tape paper with eggs to the field and in applying them to plants several problems must be dealt with, such as the wind, overheating of eggs in the carrying container, injury and dislodgement of eggs when large volumes are transported in containers, and the requirement of intensive labor for applying individual strips at each site or to each plant. Finally, the '113 device only operates at one speed and is regulated by the slit size in the bottom of egg bin and by vibrator 3.

U.S. Pat. No. 4,260,108 discloses a device for airborne release and broadcast of loose insect eggs. The disadvantages of this technique are similar to the disadvantages of the manual distribution of eggs discussed above i.e., the eggs do not necessarily fall onto the plants.

While various devices have been developed for the delivery of beneficial insect eggs to agricultural commodities, there still remains a need in the art for a more effective device for economically applying large quantities of predaceous insects, with equal distribution, to pest infested plants. The present invention provides a simple, cost effective, alternative strategy for delivering eggs of any predaceous insect which is different from the prior art devices and solves some of the problems associated with the prior art devices.

SUMMARY OF THE INVENTION

It is therefore, an object of the present invention to provide a device for attaching beneficial insect eggs to string.

Another object is to attach beneficial insect eggs to a string, which is then directly applied to plants as it feeds from a device, without the need for additional methods of attachment.

A further object of the invention is to attach eggs of beneficial insects at predetermined intervals on a string over a long distance in order to avoid cannibalism since most predaceous insects will prey on the first available food.

It is also an object of the present invention to provide a method for disseminating eggs of beneficial insects to agricultural commodities.

A further object of the present invention is to provide a biocontrol agent preparation for use on agricultural commodities.

Further objects an advantages of the invention will become apparent from the following description.

BRIEF DESCRIPTION OF THE DRAWINGS

FIG. 2 shows a front view of the spool of string 30, the string supply housing 2, and the supporting L-shaped bracket which make up the string delivery system (SDS).

FIG. 11a shows a side view of a glue application system (GAS) 12.

FIG. 11b shows detail of the wick device 13 of GAS.

FIG. 13a shows a left side view of string tensioner 46 including string guide 155b and string tensioner plates 146a.

DETAILED DESCRIPTION OF THE INVENTION

Figure 1A:
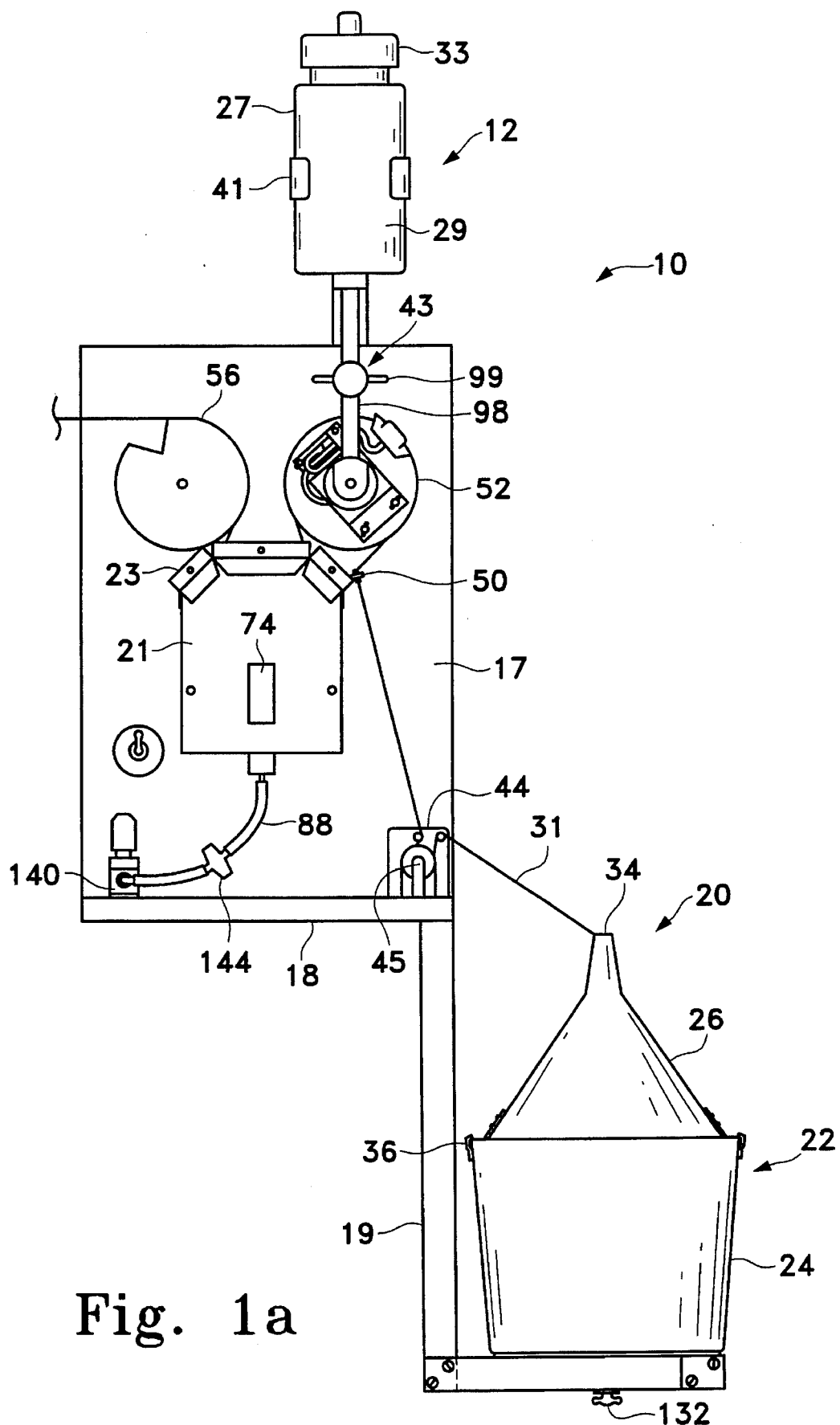
FIG. 1a shows a front view of one embodiment of the egg attaching device (EAD) 10.
Figure 1B:
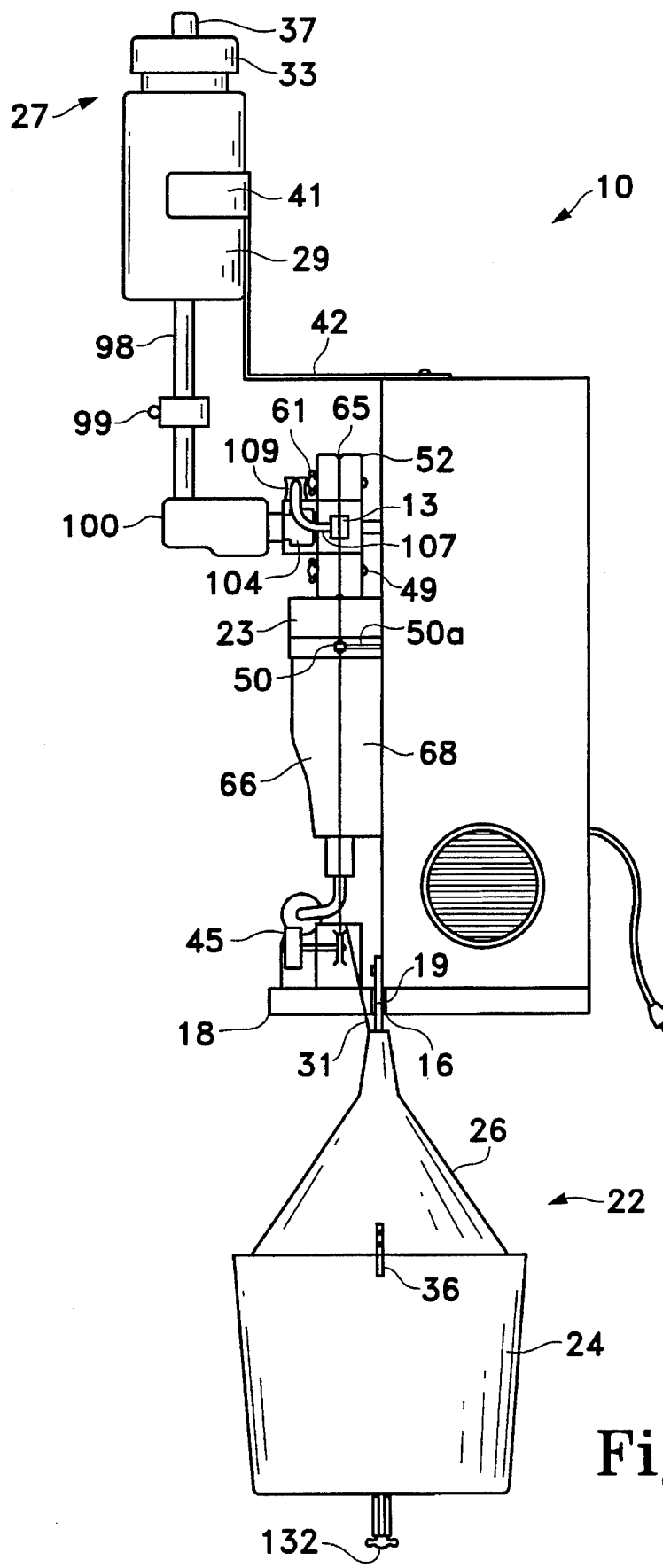
FIG. 1b shows a side view of one embodiment of the egg attaching device (EAD) 10.

Beneficial insect egg attaching devices (EADs) incorporating the features of the present invention are illustrated in FIGS. 1a–20b. EAD 10 (FIG. 1a and 1b) includes a glue application system (GAS) 2, an egg application system (EAS) 4, a string delivery system (SDS) 20, the EAD housing (EADH) 7, and the EAD base plate (EADBP) 18.

Figure 3:
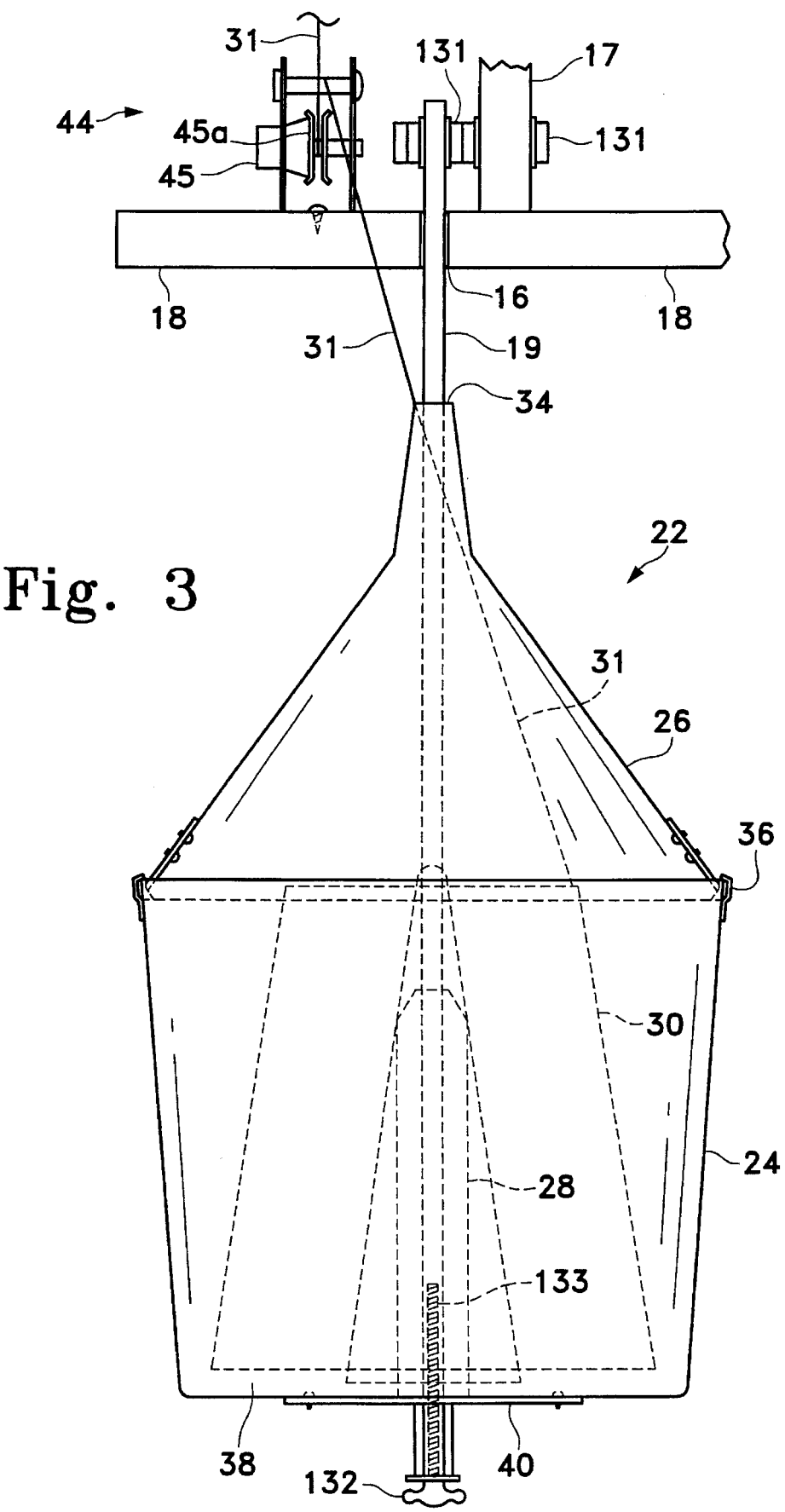
FIG. 3 shows a side view of the spool of string 30, the string supply housing 2, the supporting L-shaped bracket 9, and the tensioner assembly 44 of SDS.
Figure 4:
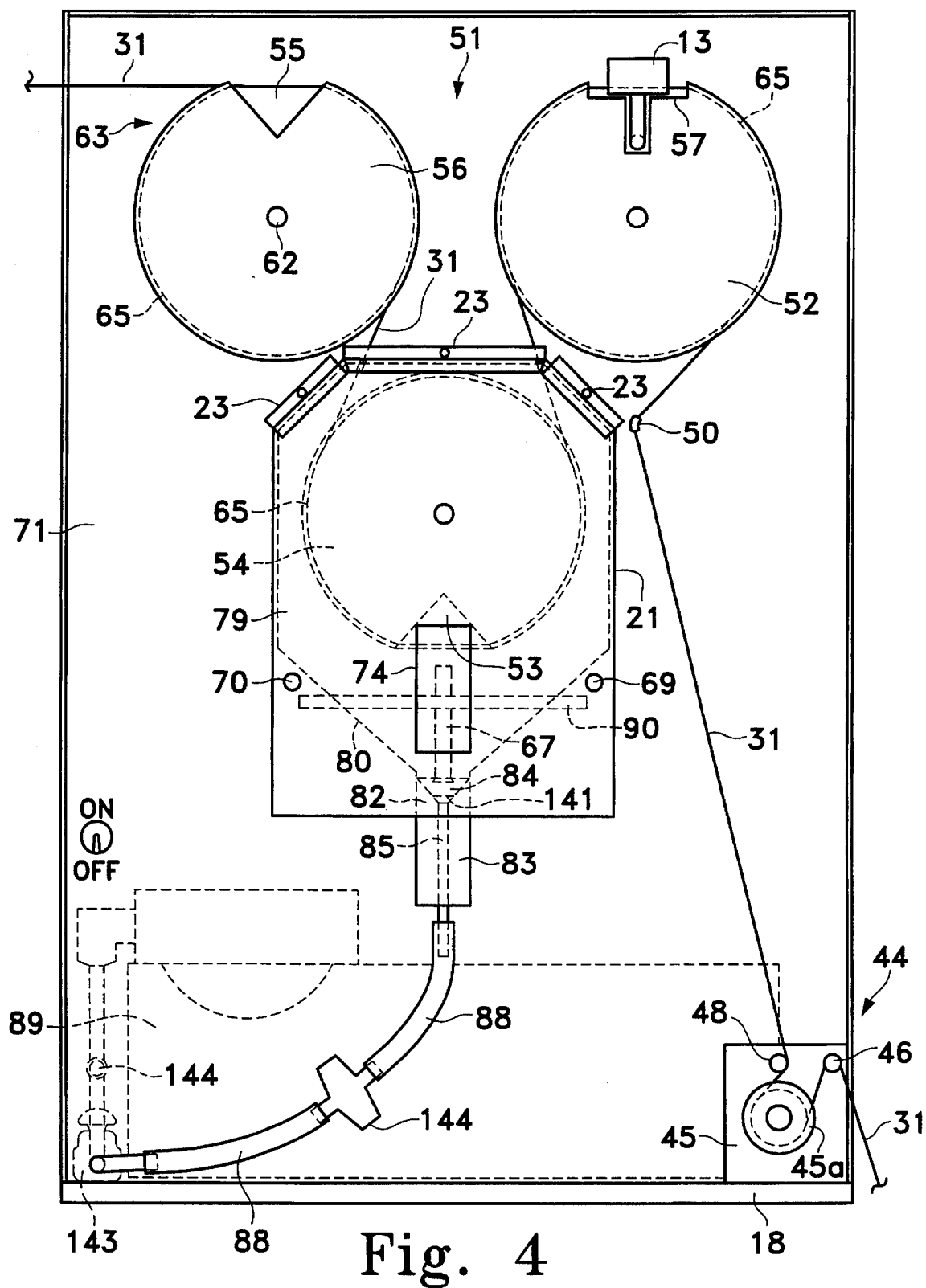
FIG. 4 shows the front view of the pulley wheel assembly the spur gear assembly 63, the string tensioner assembly 44 of SDS, the air compressor 89 of the egg application system (EAS), EAD housing 7 (EADH), and EAD base plate 8 (EADBP).
Figure 5A:
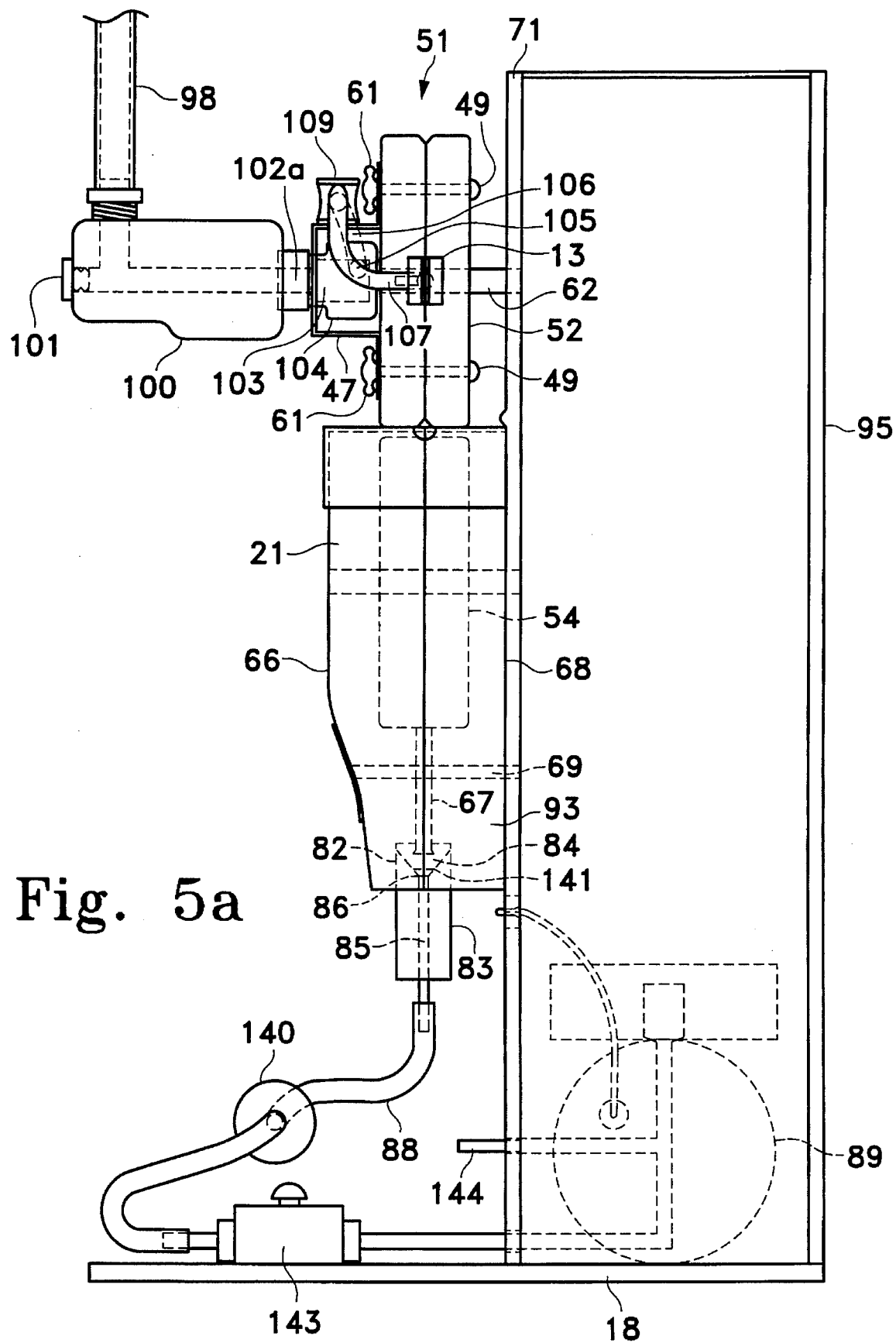
FIG. 5a shows a side view of the pulley wheel assembly 5, the air compressor 89 of EAS, EADH 7, and EADBP 8.
Figure 5B:
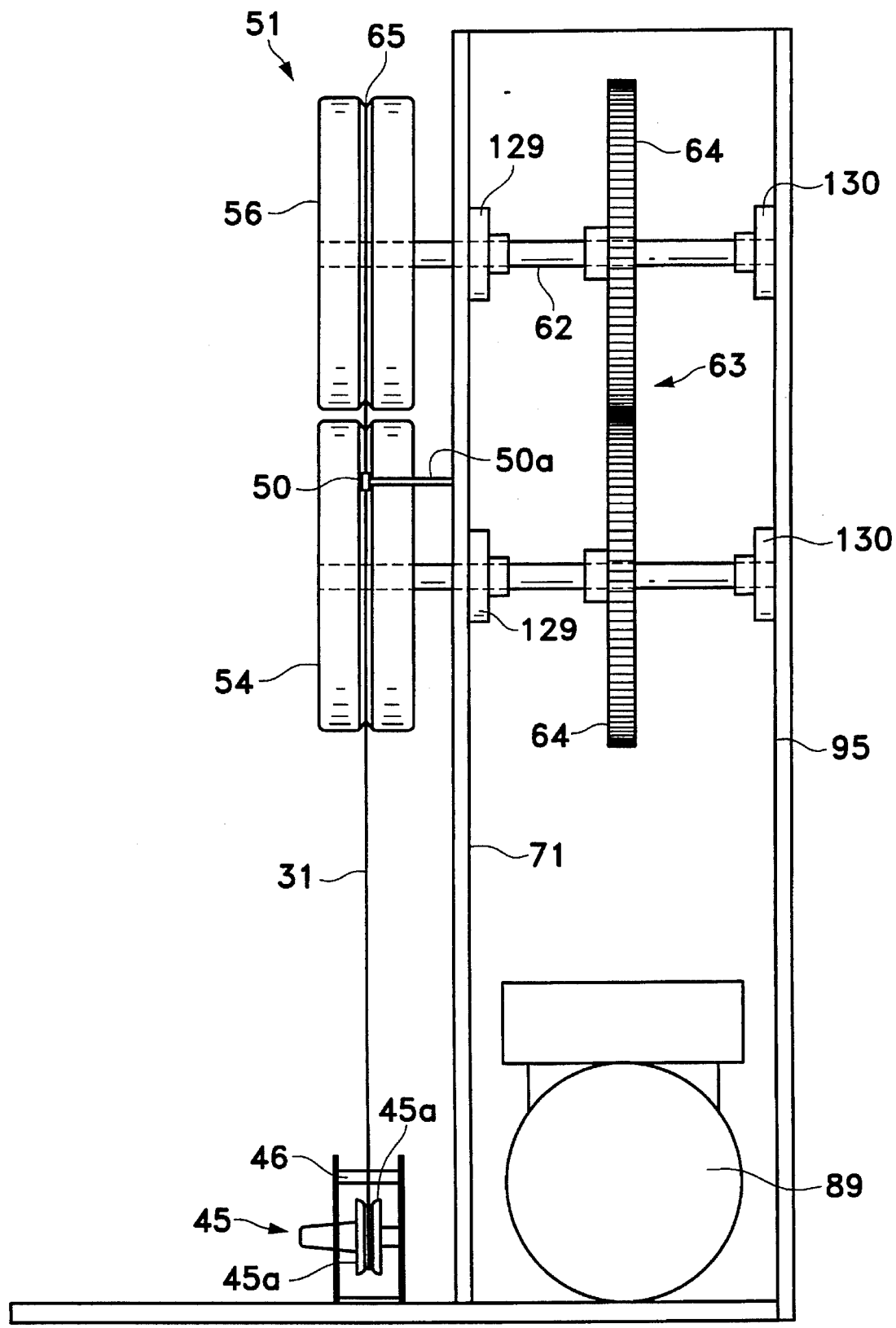
FIG. 5b shows a side view of the pulley wheel assembly 5 with details of the bearings 29, 30 and spur gear assembly 63 with spur gears 64.
Figure 6:
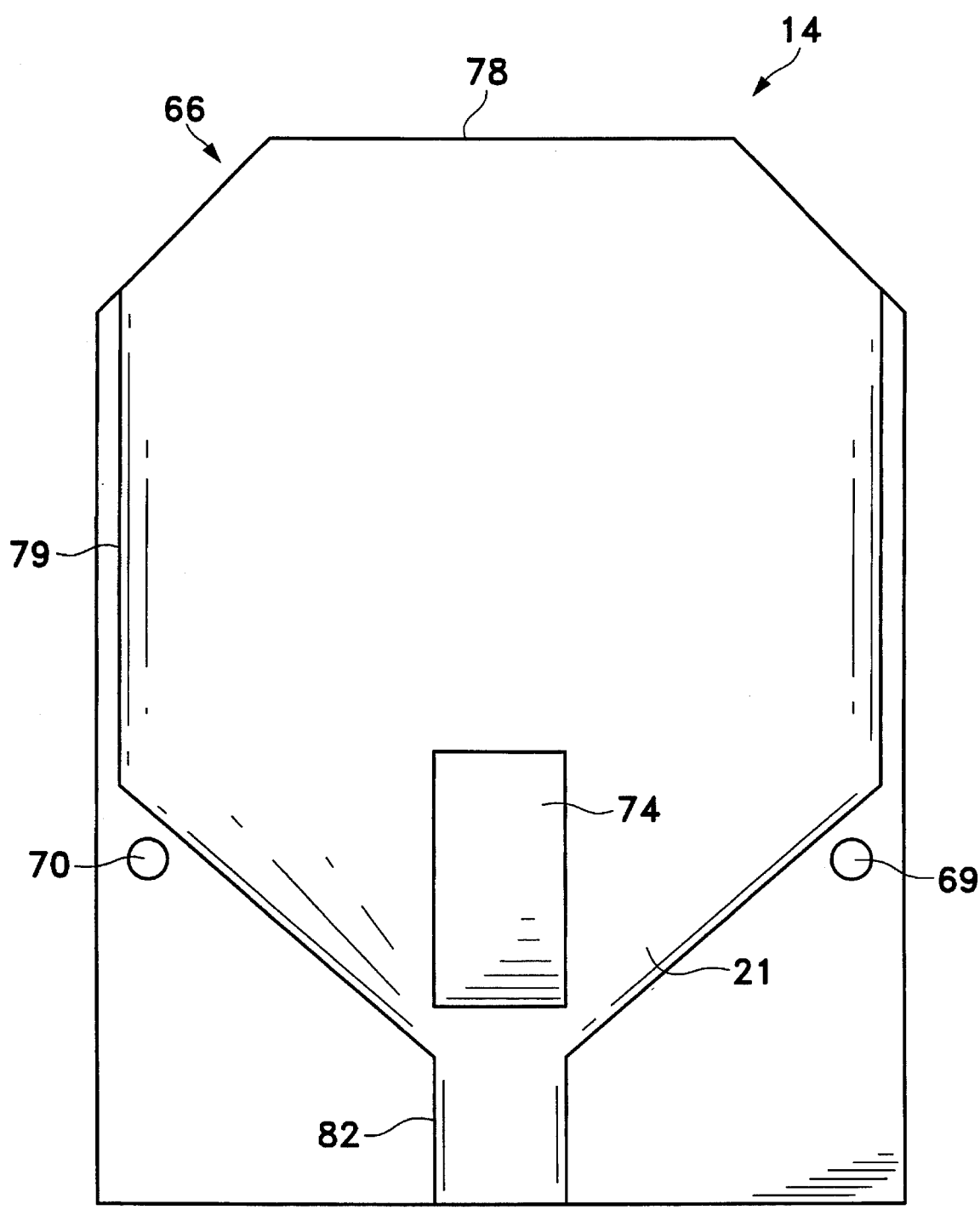
FIG. 6 shows an inside view of the front half 66 of the recirculating hopper 2 of EAS 4.
Figure 7:
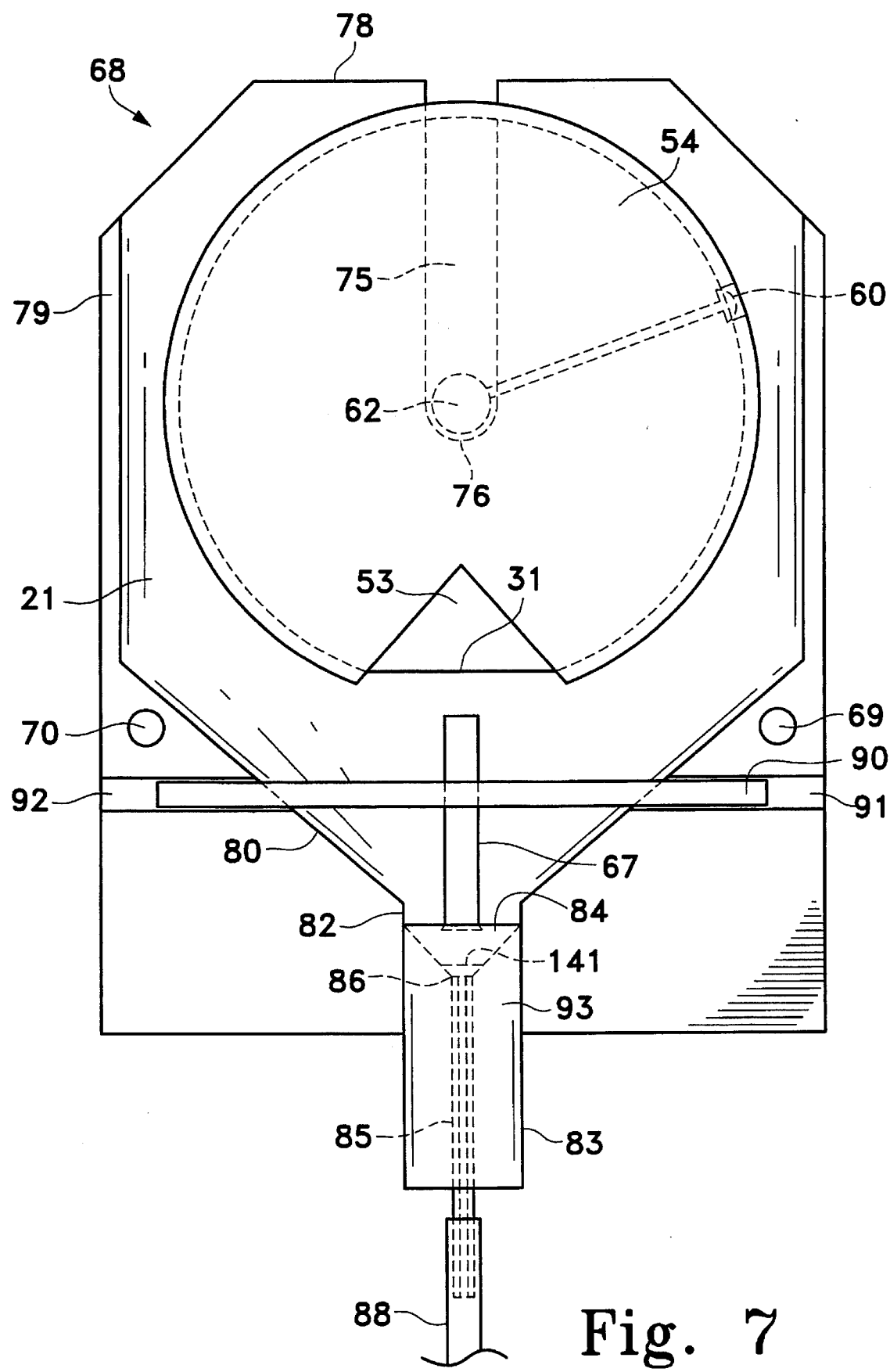
FIG. 7 shows an inside view of the rear half 68 of the recirculating hopper 2 with the front half 66 removed, the egg-lifting device 93, and egg guide 67 of EAS 4, and the pulley wheel of SDS in position.
Figure 8:
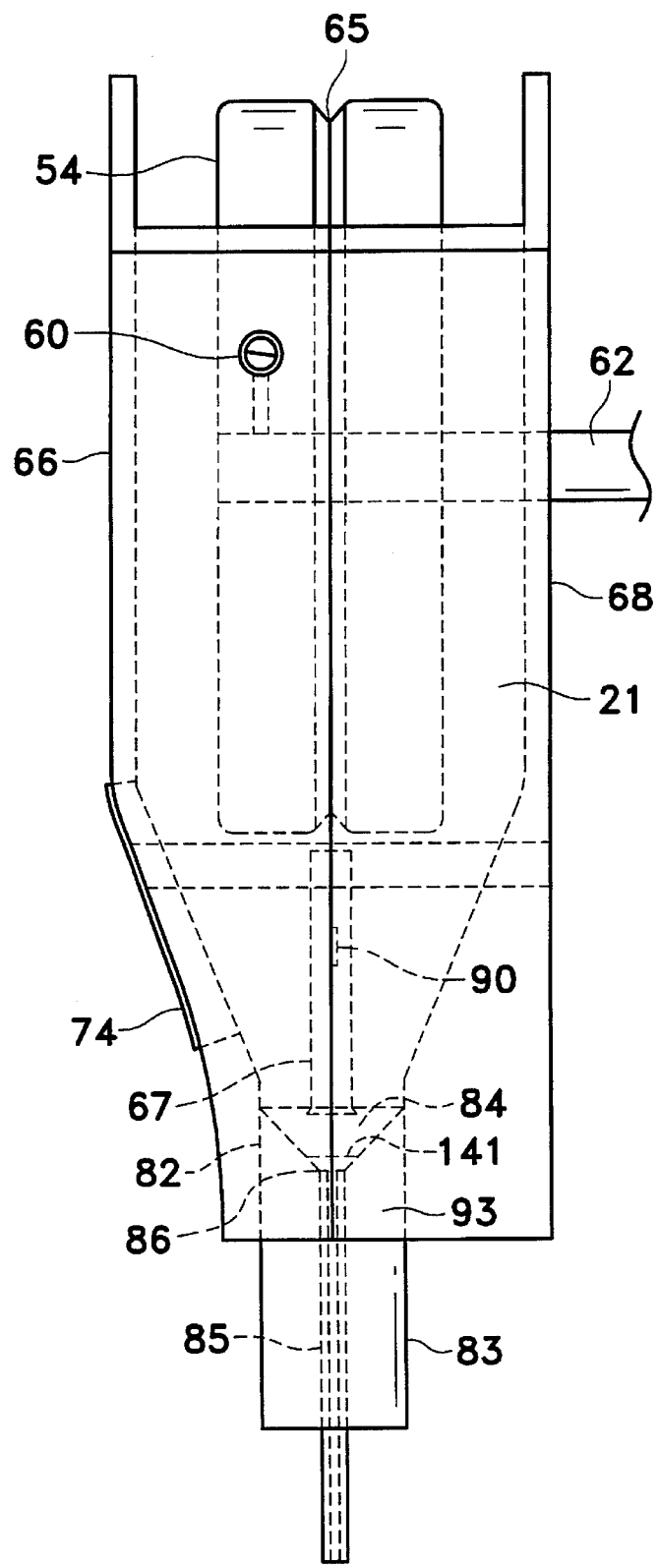
FIG. 8 shows a side view of the recirculating hopper 21, the egg-lifting device 93 and the egg guide 67 of EAS, and the pulley wheel 54 of SDS in position—the interior detail shown with broken lines.

SDS 20 (FIGS. 1–4 and 5b) is made up of string supply housing 22, a supply of string which is spool of string 3, L-shaped bracket 9 (FIGS. 2 and 3), string tensioner assembly 44 (FIGS. 3, 4 and 5b), string guide 50 (FIGS. 4 and 5b), pulley wheel assembly 5 and spur gear assembly 63 (FIG. 5b). The string supply housing 22 has a cylindrical base portion 24 and a funnel-shaped cover 26. The base portion 24 and cover 26 may be, for example, constructed of plastic. Connected to the inside bottom 38 of base portion 24 is an upwardly extending dowel 28, chamfered at it's top end. A spool of string 3 is seated onto dowel 28. Funnel-shaped cover 26 can be a funnel or any cover with an opening 34 where the string can exit the housing. The rim of cover 26 is secured to base portion 24 with fasteners 36. String supply housing 22 sits on and is riveted to housing plate 40. As shown in FIGS. 2 and 3, a shaft 133 threaded at two ends secures the dowel to the bottom of the housing 22 and to L-shaped bracket 19. The dowel and housing are releasably attached at the horizontal leg of the bracket 19 by the threaded shaft and wing nut 132. The vertical leg of the L-shaped bracket is hingedly attached to front of EADH by bolt and bushing fasteners 131. The L-shaped bracket is locked into place by a notch 16 in the EADBP 18. This arrangement allows the I-shaped bracket 19 to be rotated upwardly for storage and transportation purposes.

String tensioner assembly 44 is located directly above string housing 22 and is mounted on EADBP 18 (FIGS. 3, 4, and 5b). It includes two parallel drag bars 46 and 48, approximately one inch apart and located just above tensioner 45, made of any suitable material and are generally stainless steel. String tensioner assembly 44 also includes heavy duty variable control sewing machine tensioner 45 which includes tensioner plates 45a (FIG. 5b).

String guide 50 (FIG. 4) is located directly beneath glue pulley wheel 52 and is held in place by a stand off 50a (FIG. 5b) mounted on the front panel of EADH 17. It guides string from the spool 30 and tensioner assembly 44 to wheel 52 and ensures that the string is accepted into pulley V-groove 65 in the pulley.

The pulley wheel assembly 51 (FIGS. 4, 5a, and 5b) feeds string 31 through EAD 10 and is made up of a glue pulley wheel 52, a recirculating hopper pulley wheel 54, and a final guide pulley wheel 56. The circumferential surface of each wheel, generally constructed of a phenolic resin, has a V-groove 65. The glue pulley wheel 52 (FIG. 4) has a T-shaped slot 57 cut into its radial surface just below its circumferential surface and is approximately about 1⅞ inches wide by ⅝ inch deep. This is the wick device 13 mounting location. Recirculating hopper pulley wheel 54 and final guide pulley wheel 56 each have a V-slot 53 and 55, respectively, on their radial surface just below their circumferential surface which are approximately about 1⅞ inches wide by ⅞ inch deep. Pulley wheel 52 (FIG. 4) is located just above string guide 50 and above and to the right side of recirculating hopper 21. Pulley wheel 54 is centered below wheels 52 and 56 and within the upper portion of the recirculating egg hopper 21. Above, and to the left of wheel 54 is pulley wheel 56. The V-grooves of all three pulley wheels are aligned. The pulley wheels are each attached to axle rods 62 that are movably attached to front and rear housing panels 71 and 95 by flange mount bearings 129 and end bearings 30 (FIG. 5b). The pulley wheel assembly is synchronized by the intermeshed spur gear assembly 63, made up of three spur gears 64, each located behind a pulley and within the EADH 17. A set screw 60 (FIGS. 7 and 8) extends through each pulley wheel to the axle rod 62. The wheels are synchronized and locked in place with the set screw so that a point on the string at the center of wick device 13 will also be centered over slots 53 and 55 of pulley wheels 54 and 56, respectively, when the string passes around the pulley wheels. This prevents adhesive and eggs from contacting the pulley wheels and crushing the eggs.

Figure 9A:
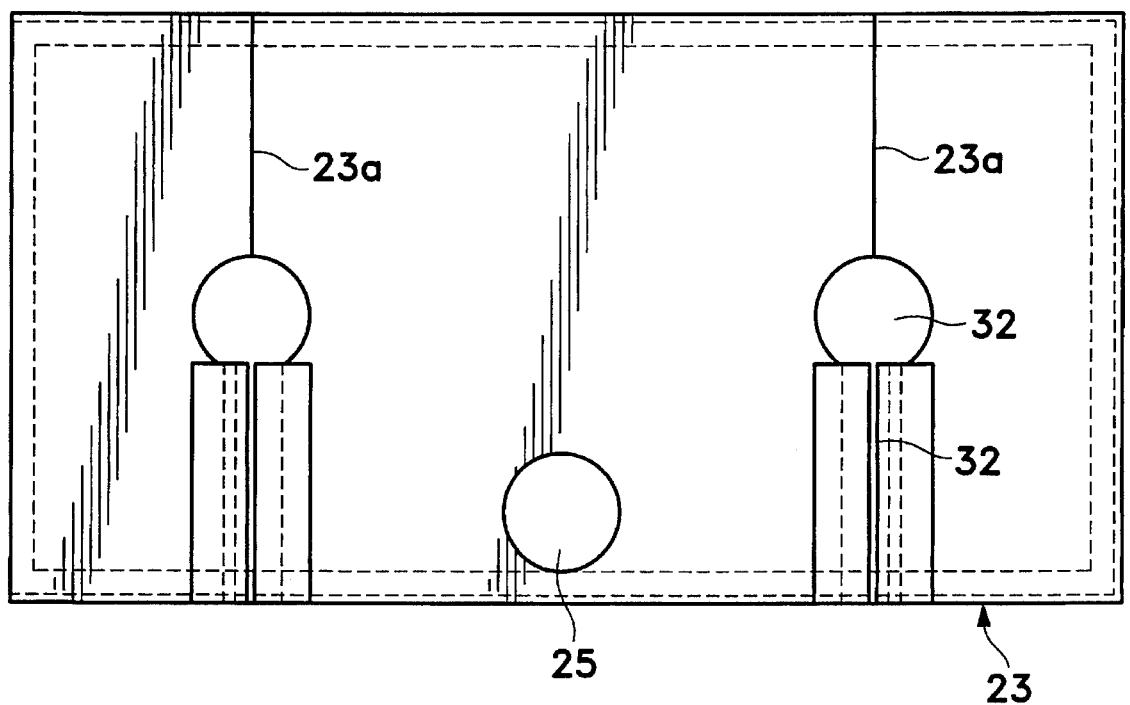
FIG. 9a shows a top view of hopper cover 23 with cover opening 25 and string openings with slots 32.
Figure 9B:
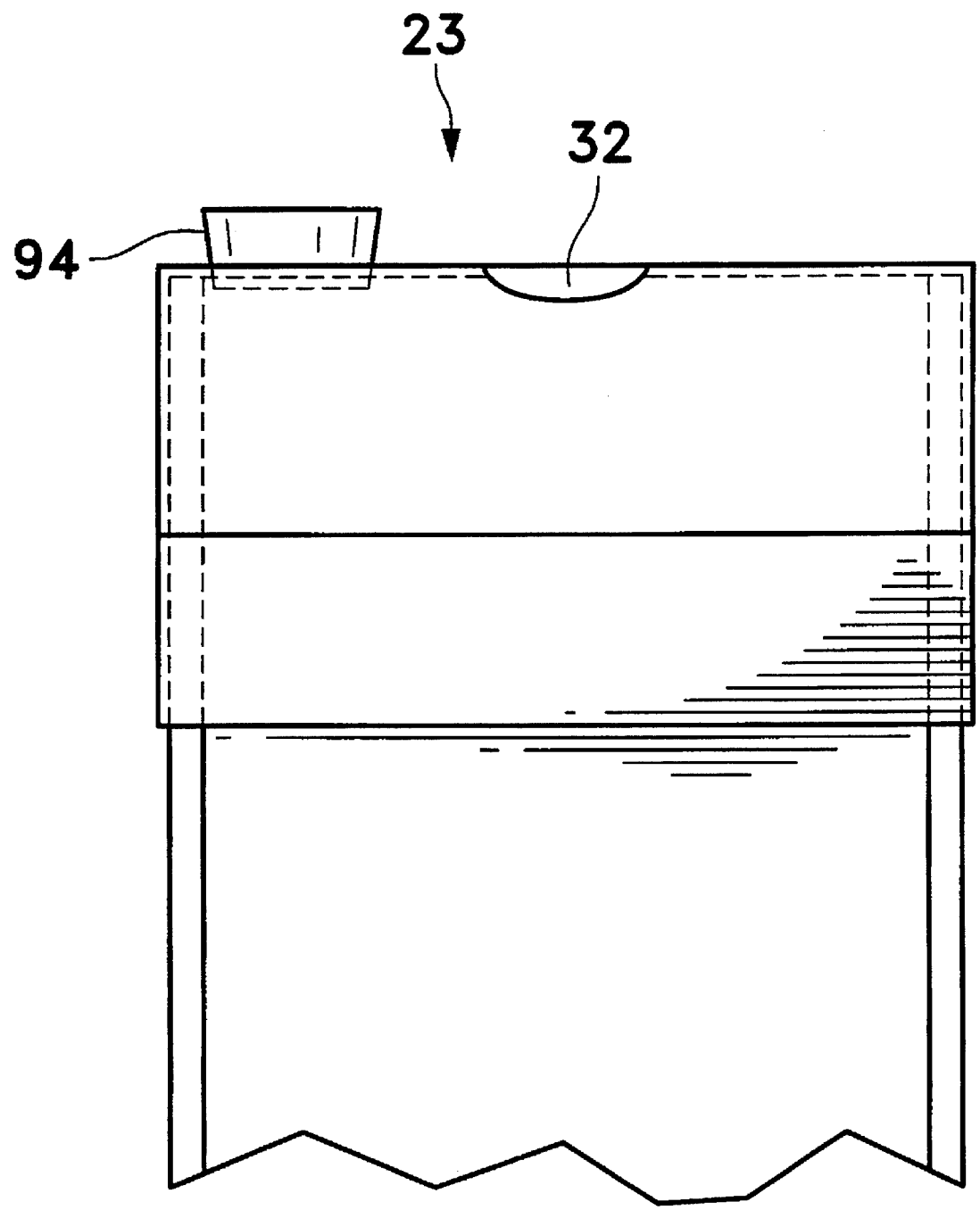
FIG. 9b shows a side view of hopper cover 23 with string opening 32 and stopper 94.
Figure 10:
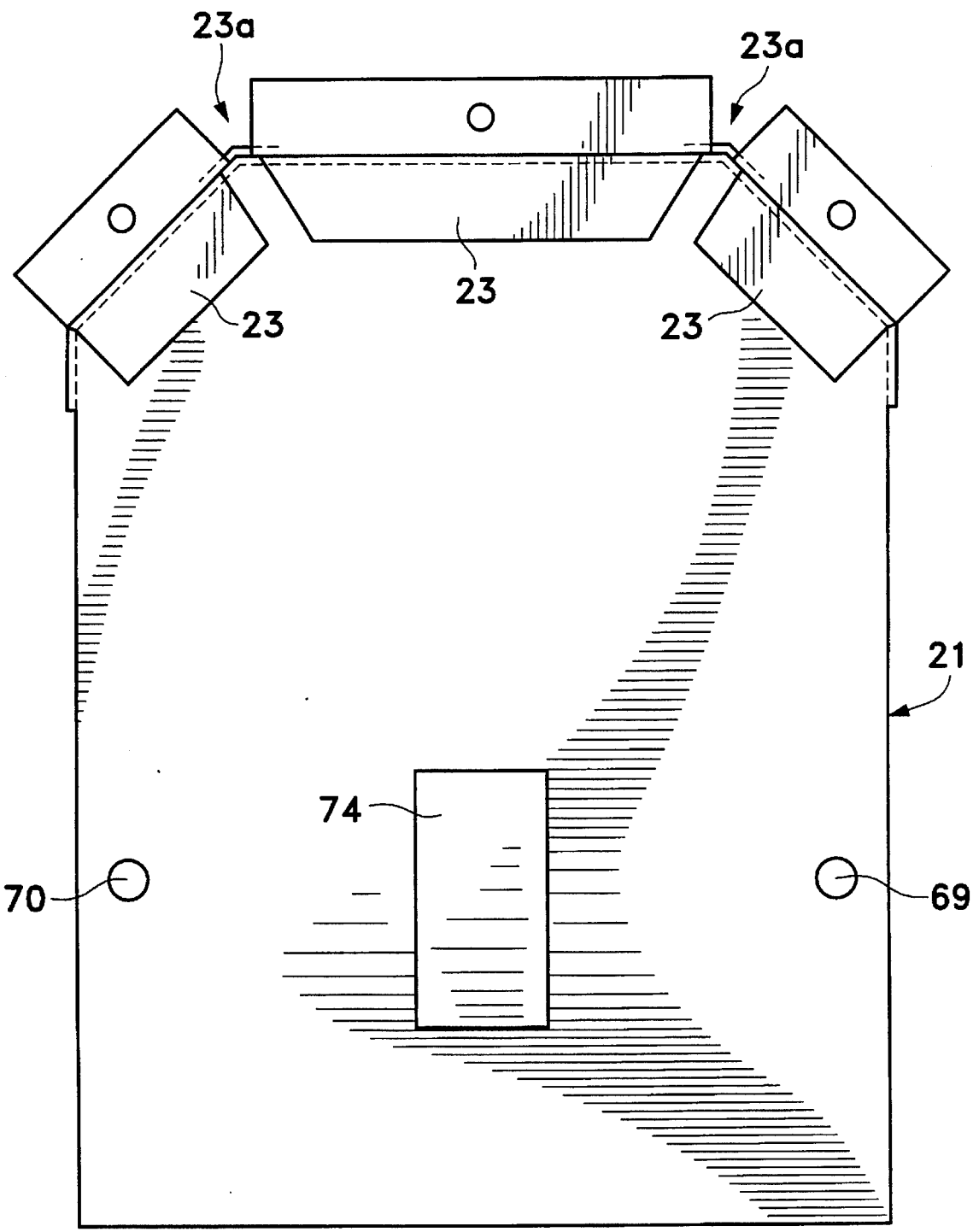
FIG. 10 shows a side view of hopper 2 with cover 23.

Recirculating hopper 21 (FIGS. 4 and 8) is centered and located below pulley wheels 52 and 56. It is made up of front- 66 (FIG. 6) and rear-half 68 (FIG. 7) of hopper, egg-lifting device 93 (FIGS. 7 and 8), and a hopper cover 23 (FIG. 9a, 9b, and 10). The hopper is generally cast from a plastic resin while the cover is generally constructed of sheet metal. Cover 23 has two 45-degree folds 23a (FIGS. 9a and 10) to fit the shape of the top of recirculating hopper 21. The cover 23 is slotted from the front-side to two openings 32 (FIGS. 9a and 9b) centered above the V-groove of pulley wheel 54 for the string to enter and exit the hopper as it passes around pulley wheel 54. Centered on the top surface of hopper cover 23 is cover opening 25 (FIG. 9a) into which a small funnel can be inserted to load hopper 21 with eggs. A small stopper 94 can be used to close opening 25 (FIG. 9b).

From a front view, recirculating hopper 21 and hopper cover 23 are generally irregularly hexagonal in shape but can be of any possible shape and made of any suitable material. It consists of front half 66 (FIGS. 6 and 8) and rear half 68 (FIGS. 7 and 8) which are held together by a bead of caulking that allows for separation of the two parts for adjustment of egg guide 67. When hopper 2 is constructed of plastic, it should be painted with aluminum or other suitable paint to eliminate static electricity build-up caused by the recirculating eggs. Recirculating hopper 21 is removably mounted and encases pulley wheel 54 from the lower side. Hopper 21 has screw mounting holes 69 and 70 on each side which receive mounting screws for attaching the recirculating hopper 21 to the front panel of EADH. When the two screws are removed, hopper 21 drops downward from the hopper cover 23. The front half 66 of hopper 21 has a rectangular shaped clear viewing window 74 (FIGS. 6 and 10) located just above the internal area where funnel-shaped top 84 of dowel 83 is located. The rear portion 68 of hopper 21 has a vertical slot 75 (FIG. 7) with a curved base portion 76 for receiving pulley wheel axle rod The inner-upper edge 78 of hopper 21 (FIGS. 6 and 7) is horizontal with lateral 45 degree outwardly sloping edges which intersect with inner vertical side walls 79. The inner basal walls 80 inwardly slope from walls 79 at approximately about 45 degrees. The four walls slope downwardly to a cylindrical shaped cut-out 82. Egg-lifting device 93 (FIG. 7) fits in cut-out 82. Device 93 is constructed of a ¾-inch dowel 83, and a ⅛-inch air supply tube 85. An air supply line 88, connects the ⅛ inch tube with the air compressor 89 (FIGS. 4 and 5a). Dowel 83, placed in cut-out 82 is generally made of wood and has a longitudinally centered ⅛ inch bored hole. The top 84 of dowel 83 is funnel-shaped. Inserted through the longitudinal hole of dowel 83 is tube 85 which can be made of any suitable material and is generally copper tubing. Tube 85 extends upwardly through to base 86 of funnel-shaped top 84 of dowel 83 and downwardly through the dowel creating a continuous airway through dowel 83. A small retaining screen 141 is glued by its edge to the inside of top 84 just above the upper end of tube 85. Screen 141 prevents eggs from falling into ⅛ inch air supply tube 85. Located approximately halfway between the bottom of pulley 54 and top of dowel 83 is sheet metal support which inserts into recesses 91 and 92 located on the outer face of the rear half 68 of hopper 21. Support 90 holds tube-shaped egg guide 67 by friction in a vertical position and allows for lateral and vertical adjustment of the guide. Egg guide 67 is positioned directly above ⅛ inch air supply tube 85. Guide 67 is made of any suitable material and is generally brass. The lower end, positioned just inside funnel portion of dowel 83, is flared. The upper end of guide 67 extends to just below the bottom of revolving pulley wheel 54. Attached to lower end of tube 85 is air supply line 88. Line 88 can be made of any suitable material and is generally TYGON tubing. The other end of tube 88 is attached to a friction fitting from the air regulating needle valve 143. Inserted in line 88 and between needle-valve 143 and ⅛ inch air supply tube 85 is filter 140. Filter 140 can be any filter and is generally a small automotive fuel filter. It prevents insect scales from being sucked by back-pressure into the needle-valve and the air compressor 89. Needle valve 143 is for adjusting air flow and regulating the flow of eggs that fountain from egg guide 67. In the air line between the needle valve 43 and the compressor 89 is located a T-outlet 144 for bleeding-off excess air produced by compressor 89.

GAS 12 (FIG. 11) is made up of a glue container 27, a glue delivery assembly 43, and the wick device 13. Glue container 27 is made up of two parts, a reservoir portion 29 and a cover portion 33. These two portions are generally constructed of a plastic but can be made of any suitable material. Glue container 27 can be attached to rear panel of the EADH (not shown) using any suitable means for attachment such as a fold-over retaining bracket 42 with a reservoir holder 41. Cover 33 has an air vent 35 with air vent closing screw 37. Reservoir 29 has modified base 96 with an opening. Attached to this opening is bung-hole fitting 97. Fitting 97 can be any fitting suitable for attachment of tubing. Generally a bung hole outlet with a threaded male connector having a barbed hose fitting is used. Attached to the bung-hole fitting 97 is the glue delivery assembly 43, through which glue is gravity fed, made up of semi-rigid reinforced tubing 98 and stopcock valve 99, pinch valve 109, and rotating union 100 all of which control the flow of glue through the tubing. Tubing 98 can be any semiflexible tubing and a reinforced plastic tubing is generally used. Stopcock 99 is inserted into the tubing between reservoir 29 and rotating union 100. The stopcock controls the initial flow of glue. Rotating union 100 allows unrestricted flow of glue without leakage or seepage. It has a removable clean-out plug screw 101 on the front side for aid in clean-up. The outlet end 102 of the rotating union 100 has a ⅜ inch locking nut 102a and ⅜ inch galvanized nipple 103 attached. Glue delivery assembly 43 is attached to pulley wheel 52 by a mounting bracket 47 using mounting bracket bolts 49 and locking wing nuts 61. Mounting bracket 47 has a centered ⅜ inch hole through which the ⅜ inch galvanized nipple 103 passes. The nipple 103 is locked onto bracket 47 by the ⅜ inch locking nut 102a on the front side of bracket 47. Galvanized cap 104 has a port 105 drilled into one side. Inserted and soldered into port 105 is a short length of ¼" tubing 106 which is made of any suitable material and is generally copper tubing. Plastic tubing 107, generally TYGON tubing, connects tube 106 with a ¼ inch elbow 108 which is generally made of copper. Tube 107 passes through pinch valve 109 located a few inches from elbow 108. Pinch valve 109 is generally made from plastic and prevents excess flow of glue onto wick device 13 when the string is not being pulled from EAD 10. Elbow 108 is held in place in pulley 52 by a set screw (not shown). Wick device 13 is pressed into elbow 108 so that the bottom of metal support 110b of wick device 13 rests on the bottom of the groove 65 in the pulley wheel 52. The slot 110a in wick 13 is aligned with groove 65 in the pulley. This allows the string to be wiped free of excess glue as it emerges from wick device 13. Wick device 13 is made up of a sheet metal U-shaped support 110 having a centered port hole in the bottom. The U-shaped support 110 is covered with the nap side of Velcro fabric 110c having a matching centered port hole. Velcro is attached to the U-support 110 by water-proof adhesive. The support 110 covered with Velcro holds glue but does not snare the string. Soldered to the bottom of U-shaped support 110 and in line with the port is a short length of ¼" tubing, generally copper tubing. It is this tubing which frictionally fits into elbow 108. This configuration allows for the rotation of locking nut a, galvanized nipple 103, galvanized cap 104, pinch valve 109, plastic tube 107, and mounting bracket 47, copper elbow 108, and wick device 13 as one unit while attached to pulley wheel 52 and to the rotating union 100.

In operation, EAD 10 (shown in FIGS. 1a and 1b) is placed on a table or on a rack of an all terrain vehicle (ATV) with approximately one inch of the right edge of EADBP 18 extending over the edge. L-shaped bracket 19 is rotated downward so that it seats in notch 16 in EADBP 18 (FIGS. 2 and 3) and extends vertically downward. String supply housing 22 (FIGS. 1–3) is mounted onto the short-legged end of L-shaped bracket 19 by passing threaded shaft 33 through the bracket. This is secured with wing nut 32. A spool of string 30 is seated on dowel 28 located within cylindrical base 24. String 31 is pulled from spool and threaded through opening 34 in funnel-shaped cover 26. Cover 26 is clipped into edge of base 24 with fasteners 36. Housing 22 protects the string from contamination by rain, irrigation water, and especially, dust and dirt. Dust and dirt will cause excessive wear to the string tensioner assembly 44 and water can cause the string to slip on the pulley wheels 52, 54, and 56. From opening 34, the string is passed over drag bar 46, underneath and between the tensioner plates 45a (FIG. 5b) of tensioner 45, and over drag bar 48 (FIG. 4). The string then passes from bottom to top through the stainless eye of string guide 50. Next, the string engages groove 65 of glue pulley 52 from the right side and passes over top of pulley 52. The string is then threaded onto recirculating hopper pulley 54 after recirculating hopper 21 is removed. Screws are removed from mounting holes 69 and 70 and hopper 21 is pulled down to give access to pulley 54. The string is threaded down through the right hand opening 32 (FIG. 9a) in hopper cover 23, around the lower edge of pulley 54, and up through the left hand opening 32 (FIG. 9a) in cover 23. The string is then passed over final guide pulley 56 from right to left and hopper 21 is replaced over pulley 54.

Proper tension of string and rotation of pulleys are tested by pulling several yards of string from the device. Proper tension and rotation will allow one to walk at a fast pace without causing the string to break. Furthermore, the string will slice into, and to the bottom of slot 110a in wick 13. Inadequate tension will allow the string to ride high in slot 110a causing inadequate application of glue. Excess tension may cause the string to break. The pulley wheels are synchronized by set screws 60 which extend through the radius of each pulley to each axle rod 62. These are loosened to adjust the pulley and then retightened to maintain the adjustment. Synchronization is accomplished by marking the string with ink at the point where glue is applied on wheel 52. Wheels 54 and 56 are then adjusted so that the marked point on the string matches the center of the V-slots 53 as it is pulled from EAD 10. The V-slots 53 prevent adhesive and eggs from contacting the pulley wheels.

Next, the device is loaded with glue (FIG. 11). The fold-over retaining bracket 42 is folded upward from it's storage position. The glue delivery assembly 43 is rotated upward to a vertical position from it's downward position so that the glue container 27 and reservoir holder 41 are mated. Before adhesive is poured into the glue container, stopcock valve 99 and pinch valve 109 are set in the closed position. Glue, usually containing a colorant for visual detection, is poured into the container 27 and cover 33 is replaced. Next, elbow 108 is seated into slot 57 of pulley 52 so that the end opening of the elbow rests flush with the flattened surface of the T-shaped slot 57. The elbow set screw (not shown) is tightened to hold elbow 108 in place taking care not to crimp the elbow by overtightening the set screw. Tubing of wick device 13 is pressed into the elbow opening until the lower side of the wick rests on the flat surface of the T-shaped slot 57 of pulley 52. Under extreme conditions of heat and humidity, reducer (shim) inserts (not shown) may be necessary to reduce the flow of glue. The reducers are inserted into the end of elbow 108 at the union with tube 107. To supply glue to wick 13, air vent screw 37 is removed, and stop cock valve 99 and pinch valve 109 are opened. Glue immediately begins to flow slowly toward wick 13. To hasten glue advancement, an accessory plastic tubing can be attached to the excess air T outlet 144 and the other end of the tubing placed over air vent 35 in cover 33. A positive pressure created by the air compressor 89 in the glue container 27 causes the glue to flow to wick 13 more quickly. Once glue has began flowing through GAS 12, pinch valve 109 is closed until operation of EAD 10 begins.

After setting up GAS 12, recirculating hopper 21 is loaded. First, the eggs of the beneficial insect are pre-screened by passing them through a sieve. Screening removes most eggs that are tangled or stuck together to prevent fouling of egg guide 67. The screened eggs are placed in hopper 21 by inserting a small funnel into the opening 25 (FIG. 9a) in the hopper cover 23 and pouring the eggs into the funnel. The volume of eggs should not exceed the height of sheet metal support 90. When compressor 89 (FIGS. 5a and 5b) is activated, a fine air stream lifts the eggs through egg guide 67 (FIG. 7) forming a fountain of eggs. Air adjustment needle valve 43 (FIGS. 4 and 5a) is adjusted so that the fountain of eggs reaches V-slot 53 of pulley 54. Too much air may cause damage to the eggs and too little will prevent eggs from reaching the string. Stopper 94 is placed in opening 25 in cover 23 to prevent loss of eggs from the hopper (FIG. 9b). Once proper egg flow is attained, compressor 89 is turned off, stopcock 99 is opened, pinch valve 109 is released, and air vent screw 37 is removed. String is pulled out of device until adequate glue is observed on the string at twelve-inch intervals. Next, compressor 89 is turned back on and eggs attach to the glue. The number of eggs adhering to each glue spot is regulated by the speed the string is pulled off the device, the amount of glue on the string, the volume of eggs lifted by the air supply, and the amount of inert filler used (if needed). Also, temperature and relative humidity may influence the flow of glue.

The device can be operated by two people to prepare individual lengths of egg-carrying string or the device can be mounted on an All Terrain Vehicle (ATV) to dispense egg-carrying strings directly onto plants.

Figure 12A:
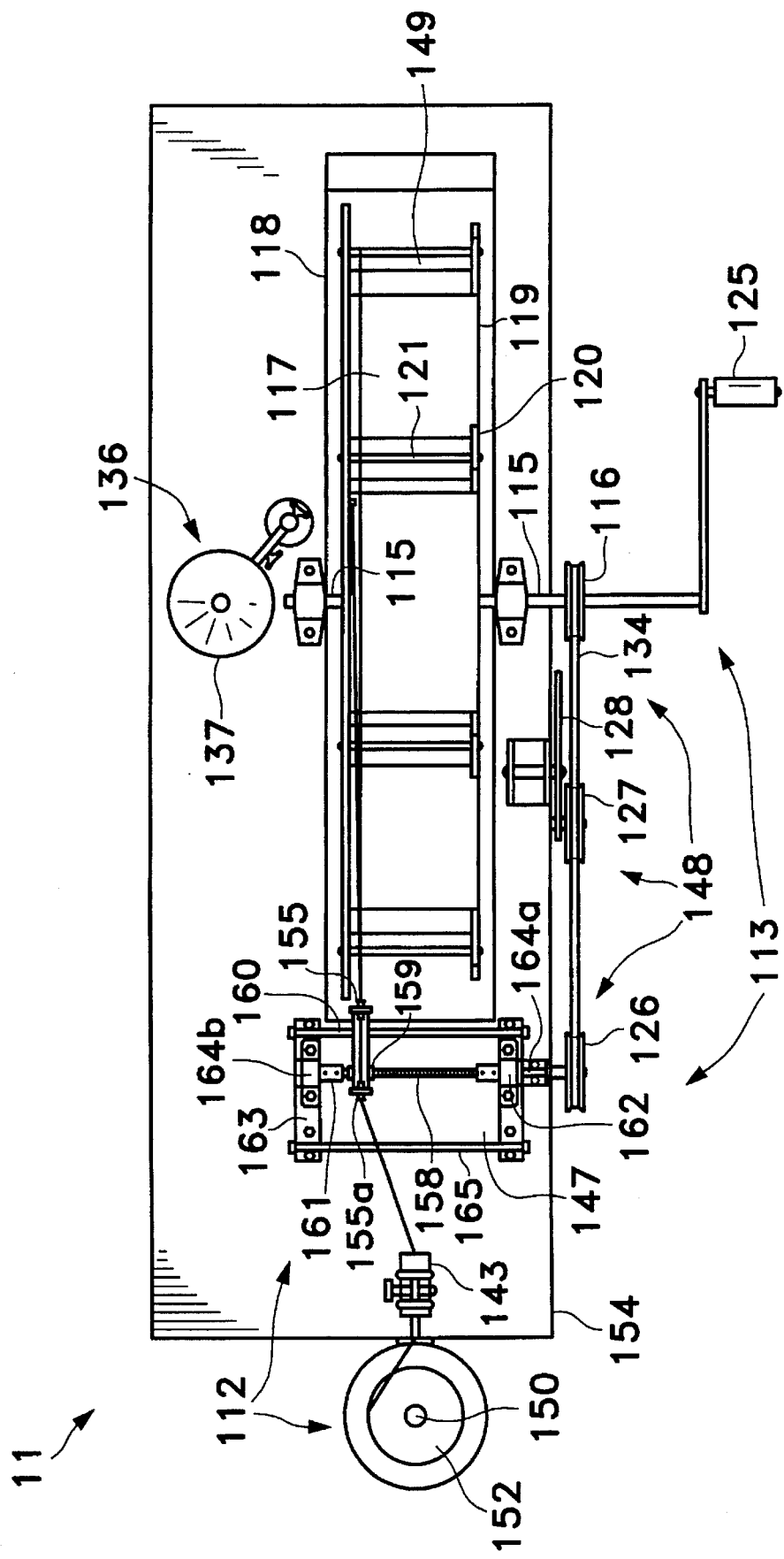
FIG. 12a shows top view of an alternative embodiment, a manual Egg Attaching Device (mEAD) 11.
Figure 12B:
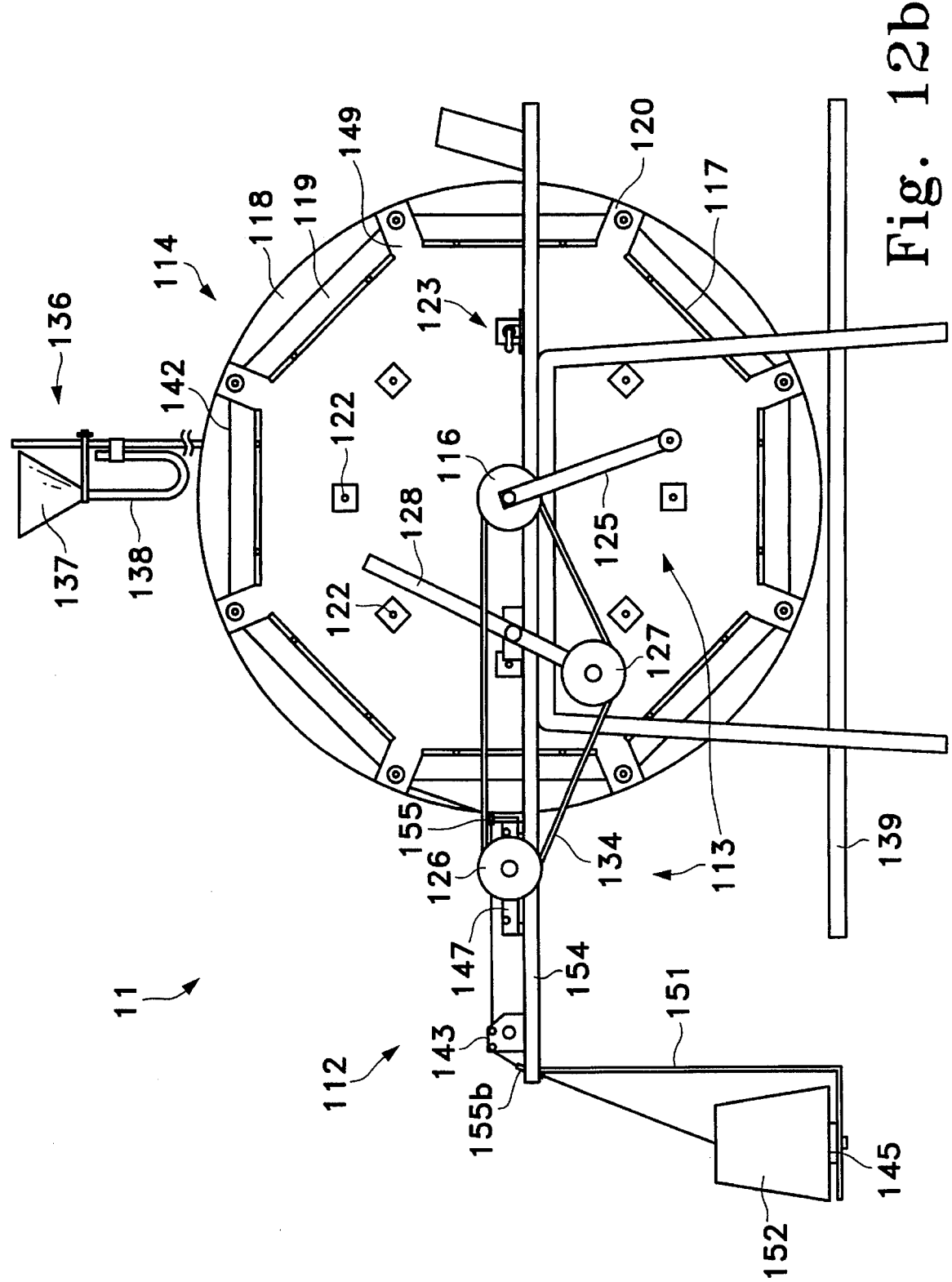
FIG. 12b shows front view of an alternate embodiment, a manual Egg Attaching Device (mEAD) 11.
Figure 13A:
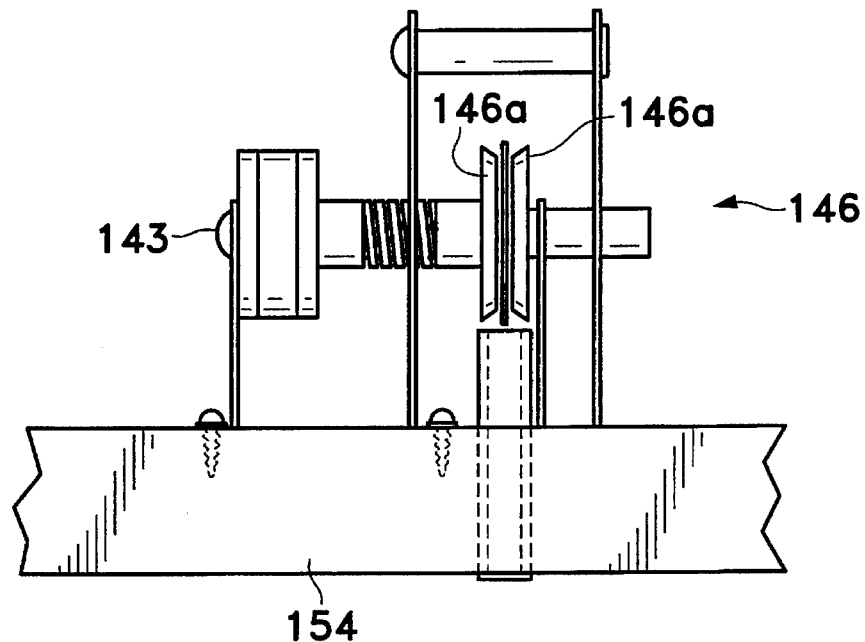
Figure 13B:
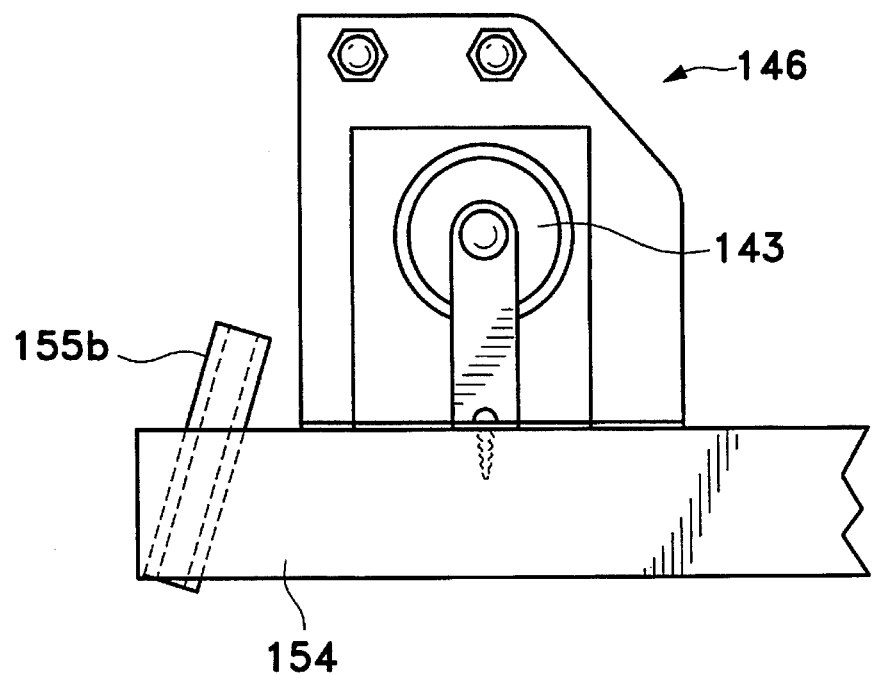
FIG. 13b shows a front view of string tensioner 146.
Figure 14:
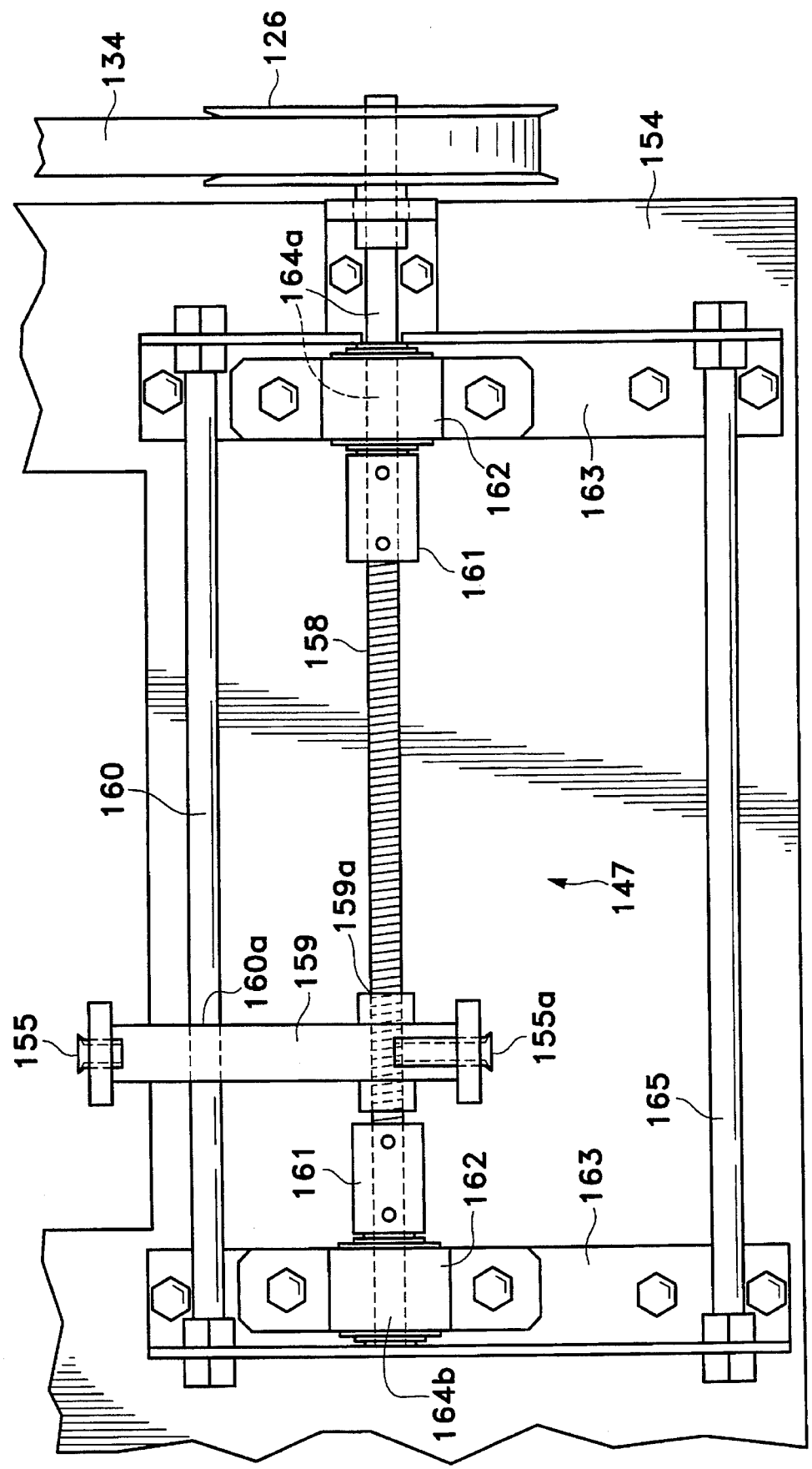
FIG. 14 shows a top view of a portion of the Pulley Wheel-String Guide System 113 (PWSGS) that includes traveling string guide device 147, string guide 155a and 155, and pulley belt 134.
Figure 15:
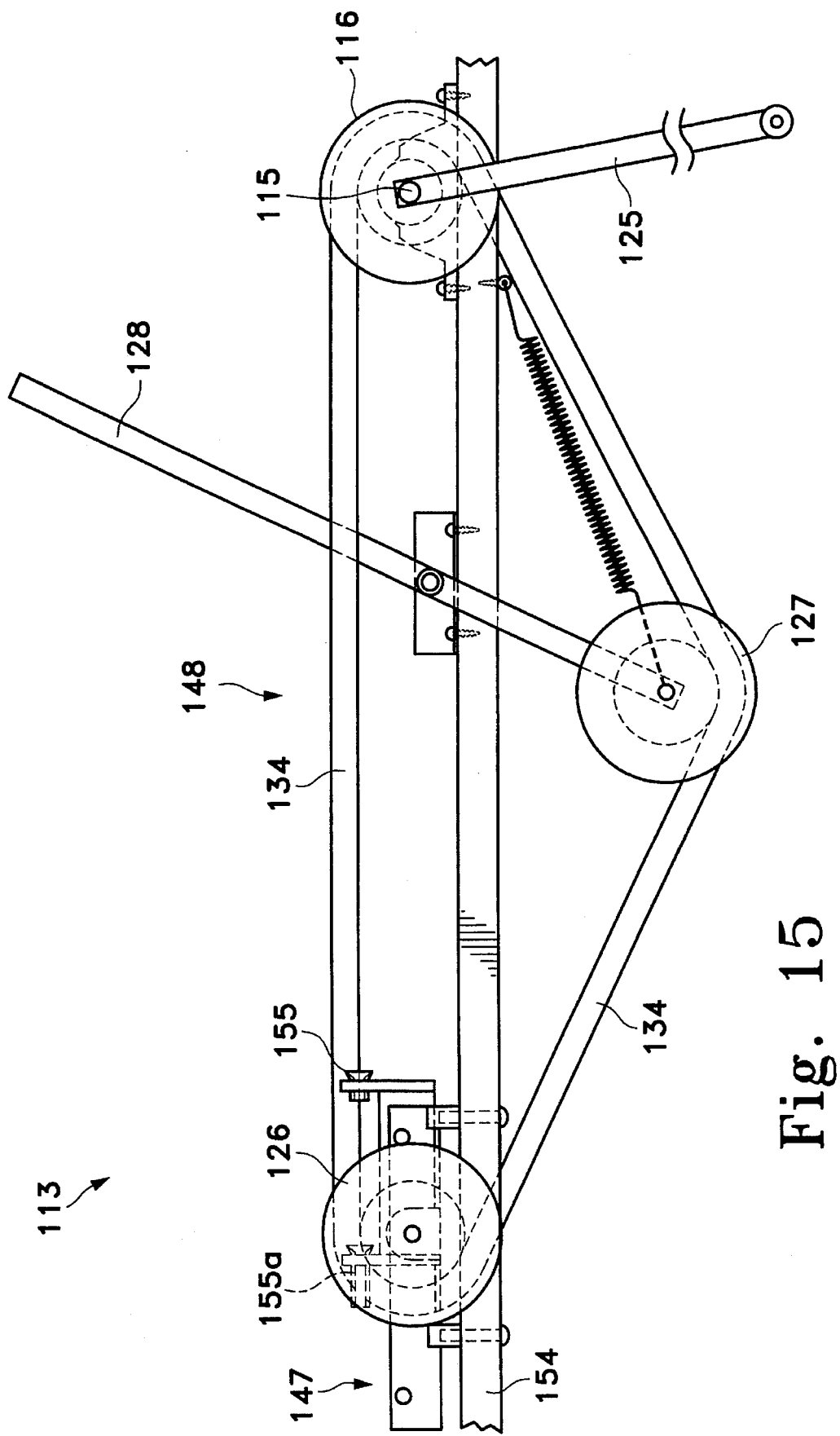
FIG. 15 shows a side view of a portion of the Pulley Wheel-String Guide System 113 (PWSGS) that includes traveling string guide device 147, pulley assembly 148 that includes pulleys 126, 127, and 116; pulley belt 134, release handle 128, axle 115, and the mechanism hand-crank 125.
Figure 16:
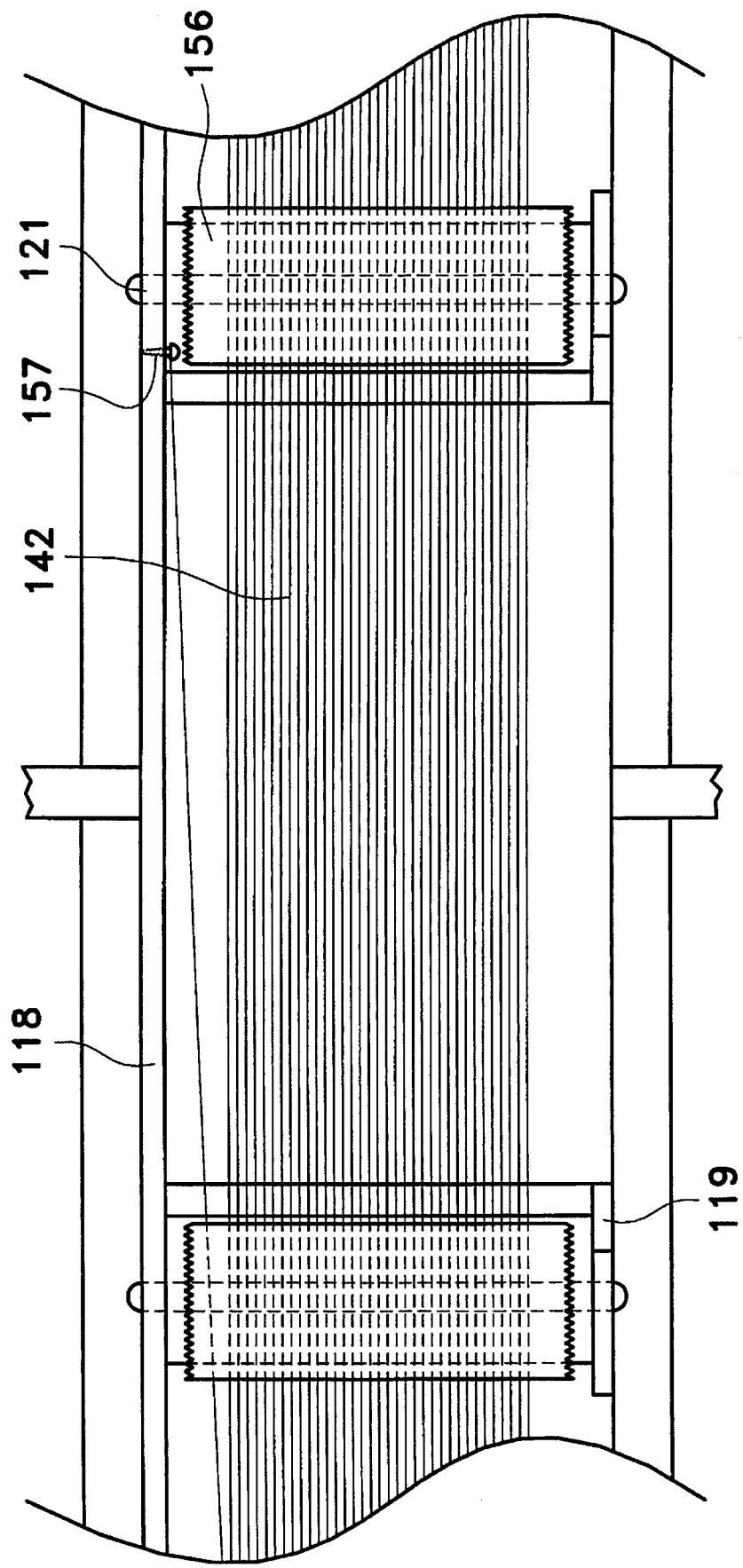
FIG. 16 shows a top view of a portion of the Drum Winding System 114 (DWS) and includes bolt of string 142, length of tape 156, circular rear panel 118, and front panel 119.
Figure 17:
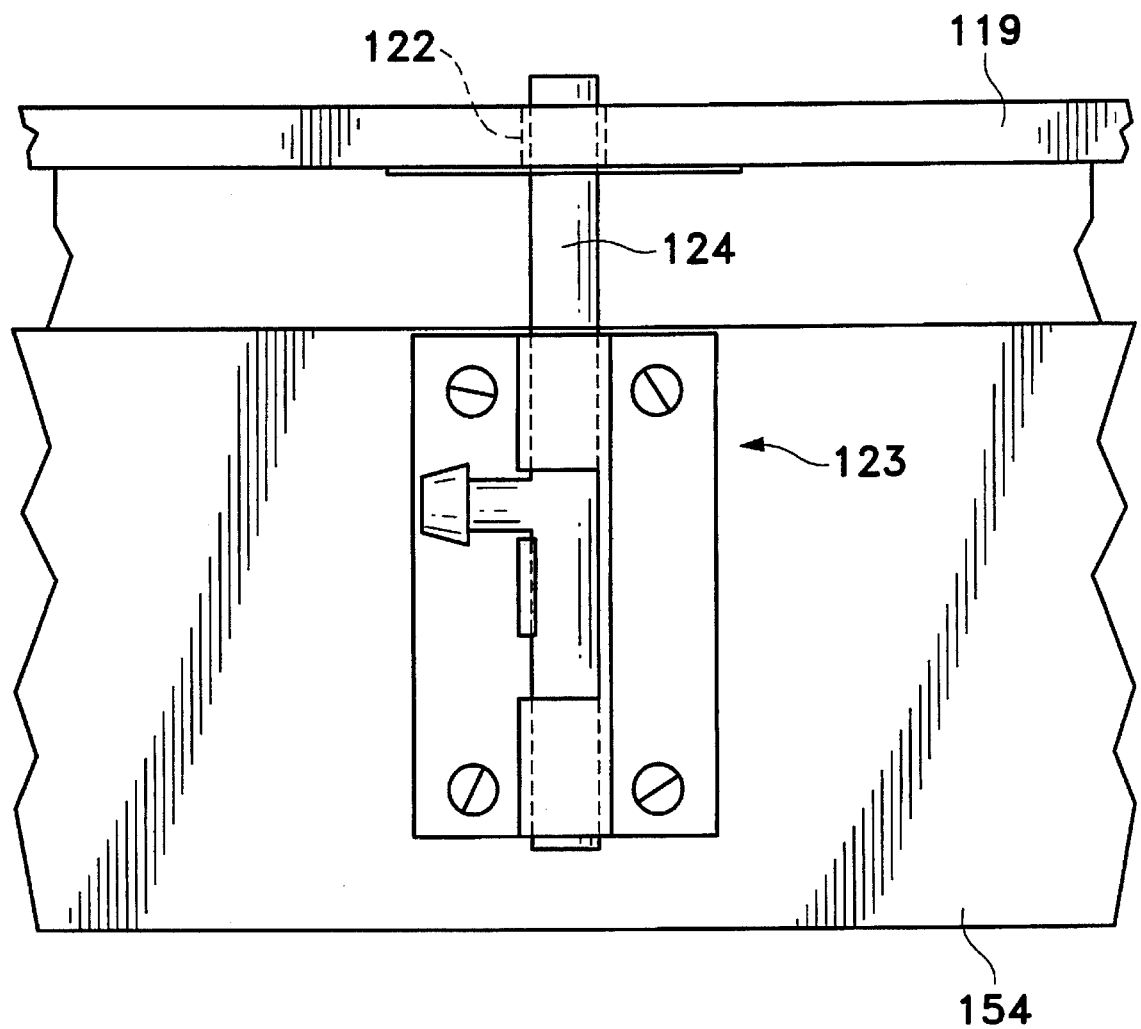
FIG. 17 shows a top view of drum holding mechanism 123 that includes sliding bolt 124 and base plate 154 (mEADBP) of mEAD.
Figure 18:
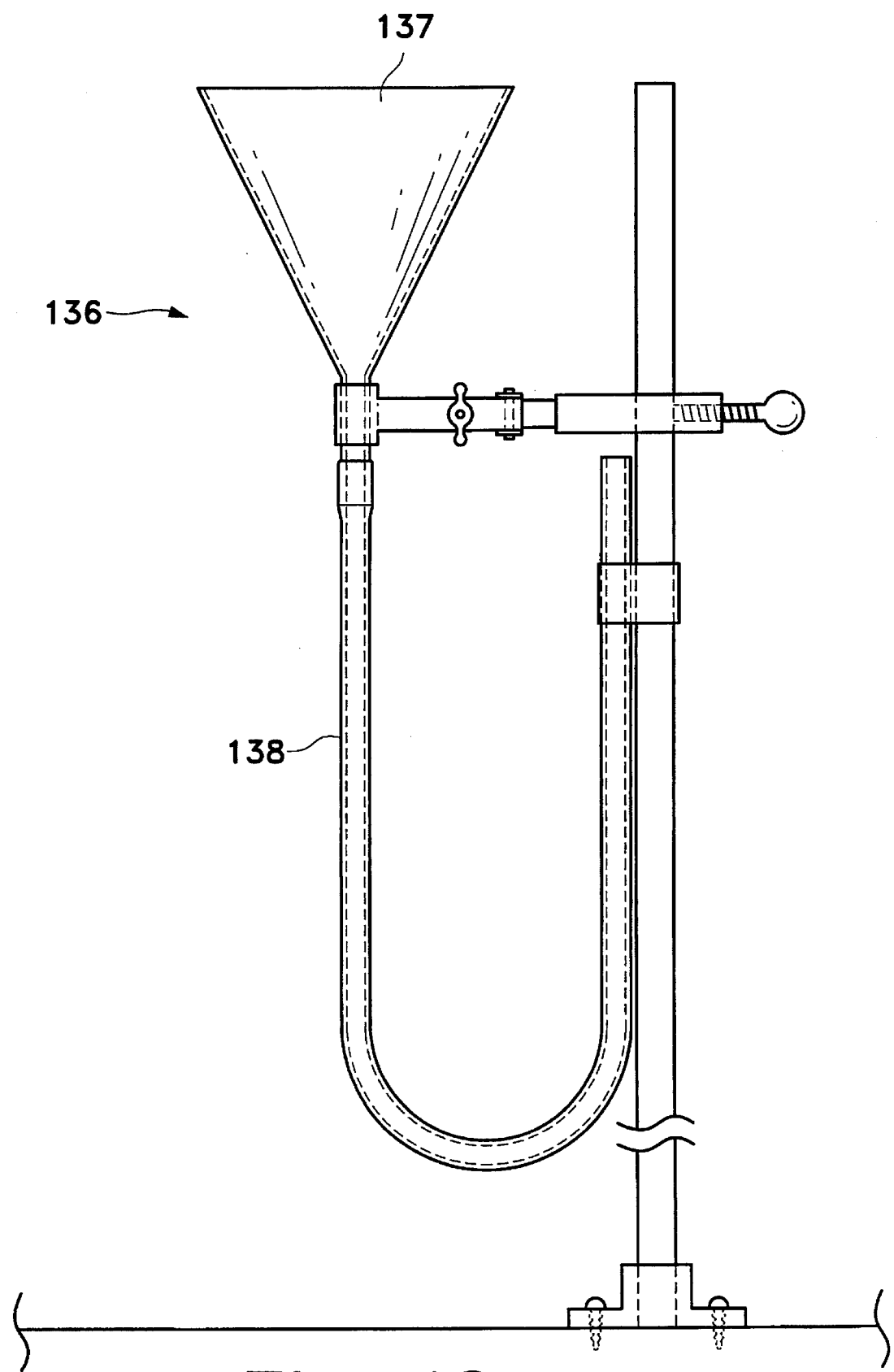
FIG. 18 shows a side view of Egg Supply System 136 (ESS) that includes funnel-shaped receptacle 137 and tubing 138.
Figure 19A:
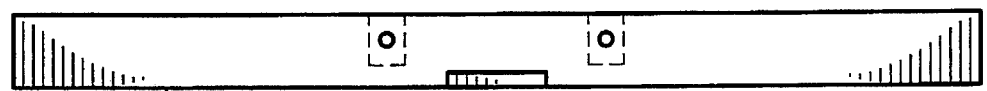
FIG. 19a shows front view of tray 166 for catching overflow of predator eggs at time of application to strings.
Figure 19B:
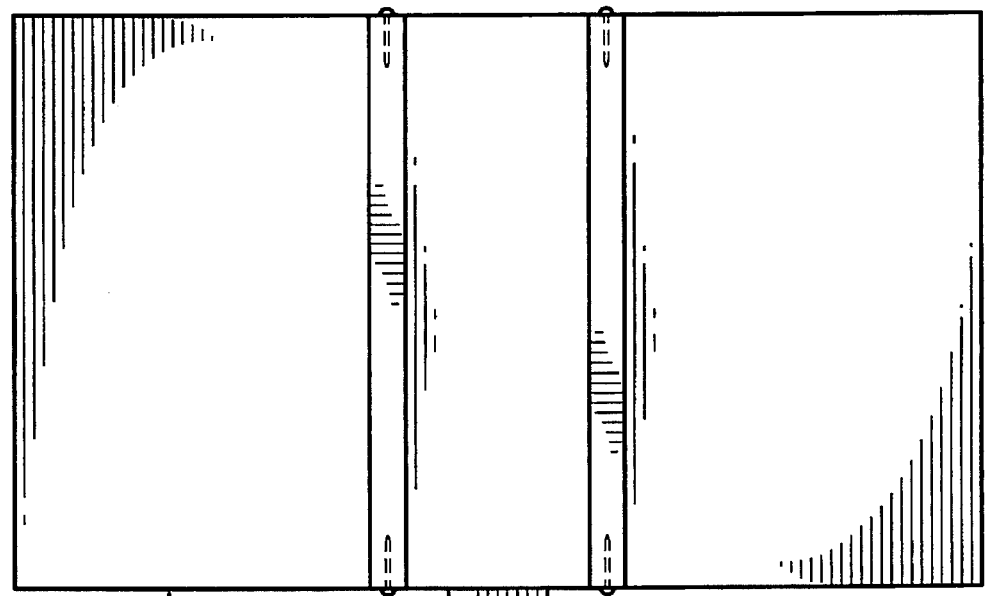
FIG. 19b shows top view of tray 166 for catching overflow of predator eggs at time of application to strings.
Figure 20B:
FIG. 20b shows end view of applicator 153 for applying glue to string on reel.
Figure 20A:
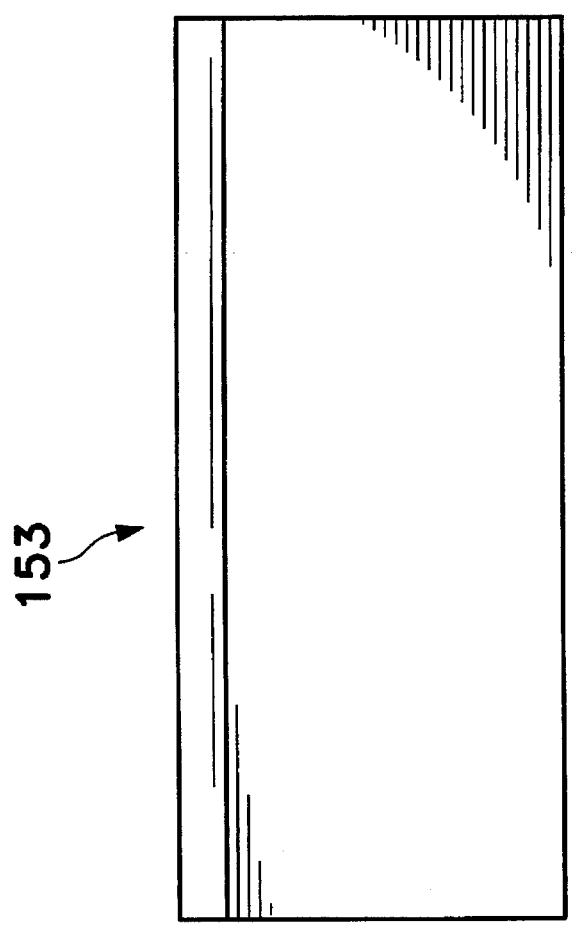
FIG. 20a shows side view of applicator 153 for applying glue to string on reel.

To prepare individual lengths of string (for example—use in greenhouse), two people are required. One person pulls the string to the desired length and the second person cuts the string to the left of pulley 56. The lengths of string are then laid along the top of each row of plants to be treated with beneficial insects. The person who cuts the string then pulls out a length of string while the second person returns to the EAD and cuts the string. This way the device does not have to be shut down between lengths. String lengths adhere tenaciously to plants in greenhouses and in the field and do not requiring securing. When pulling the string, care should be taken not to drag it across any object to avoid raking eggs from the string lengths.

When device 10 is operated from an ATV, it should be securely mounted on the left hand side of the front rack of the ATV by attachment to EADBP. With the left hand side of device 10 facing the rear of the ATV, the operator ties the string coming from pulley wheel 52 to a limb, vine, or post. The operator then drives down the crop row and the string is dispensed automatically. At the end of the row, the pinch valve is closed to prevent loss of glue and the string is cut by the operator and laid across the plants.

String pulled from EAD 10 can also be wound onto a rack for shipment by mail or for transport to the field.

When operation of the device is finished, it must be cleaned. If EAD 10 is shut down for one or two hour periods, an abbreviated clean-up procedure is followed. Stopcock valve 99 and pinch valve 109 are closed and air vent screw 37 is replaced (FIG. 11). Wick 13 and elbow 108 are removed and submerged in a container of water. The open end of tube 107 is stoppered to prevent glue from hardening in the system. To reactivate device 10, this procedure is reversed.

When EAD 10 is shut down for periods longer than 2 hours, a more intensive cleaning procedure is necessary (FIG. 11). The glue is removed from reservoir 29 by removing the container lid and swiveling the glue delivery assembly 43 downward and opening stopcock valve 99 and pinch valve 109. Most of the glue will be siphoned from the tubing and poured from the reservoir 29 and recovered for later use. The entire glue assembly (GAS) 12 is removed from pulley 52 by removing wing nuts 61 that attach the mounting bracket. The tubing is cleaned by running water through the system until it is completely clear. Wick device 13 and elbow 108 are washed in warm soapy water.

Hopper 21 is detached as previously described and excess eggs are removed. The hopper should then be cleaned with the aid of an accessory tube attached to excess air T-outlet 144 (FIGS. 4 and 5*a*), allowing the compressor to blow out any eggs and insect scales which may be lodged in the screen 141 at the bottom of the hopper 21. This is done to insure free air flow by the egg lifting device 93 to the egg guide 67. The air filter 140 prevents debris and living insects from making their way to the compressor 89.

An alternate embodiment, manual egg attaching device (mEAD) 11 is shown in FIGS. 12*a*–20*b*. Device 11 (FIG. 12*a* and 12*b*) has string supply system (SSS) 112, an egg supply system (ESS) 136, a pulley wheel and string guide system (PWSGS) 113, and a drum winding system (DWS) 114.

SSS 112 is made up of string support 145 for a spool of string 152, string tensioner 143, traveling string guide device 147, a pulley wheel assembly 148, string guide 155*b*, and drum 149 (FIGS. 12*a*, 12*b*, 13*a*, and 13*b*). String support 145 is made up of an upwardly extending dowel 150, tapered at the top end and attached to an L-shaped bracket 151 which attaches to the table below the string tensioner. Spool of string 152 sits on dowel 150.

String tensioner 143 (FIGS. 13*a* and 13*b*) is a common sewing machine tensioner with plates 146*a* and is attached to the base plate of mEAD 154 just forward and above spool of string 152. Forward of tensioner 143 is traveling string guide device 147 (FIG. 14) which allows string to be evenly placed around drum 149. As drum 149 rotates, guide 147 travels from left to right or right to left.

Guide 147 (FIGS. 14 and 15) is made up of three parallel rods 160, 158, and 165, and a perpendicular iron support 159, all mounted on an angle iron frame 163. Rod 158 is a rotating threaded rod which is fixed at each end to an axle rod 164*a* and 164*b* of the same diameter by a shaft coupling 161. Rods 164*a* and 164*b* are held in place by a set of pillow block sleeve bearings 162 mounted on frame 163. Rod 164*a* extends through the bearing support and has mounted on the end pulley wheel 126 which serves to drive guide 147. Internally threaded iron support 159 is mounted perpendicular to and onto threaded rod 158. The forward portion of support 159 is stabilized by guide rod 160. Rod 160 passes through a horizontal hole 160*a* forward of screw hole 159*a* (not shown). Rod 160 slides within hole 160*a*. Frame spacer rod 165 stabilizes angle iron frame 163. The entire pulley wheel-string guide system (PWSGS) 113 is mounted by bolts onto the base plate 154 of mEAD (MEADBP) .

Drum 149 (FIGS. 12*a* and 12*b*) is a string support and is rotatably mounted onto mEAD base plate (mEADBP) 154 by axle 115 which attaches to pulley 116 (FIGS. 12*a* and 12*b*). Drum 149 has a central octagonal-shaped core 117 with circular rear panel 118 and octagonal-shaped front panel 119. Panel 119 has eight tabs 120 which extend above the core at the corners of each side of the octagon. Rods 121 are inserted through each tab and are attached to rear panel 118. Rods 121 receive and support the string as it feeds off string guide 155. Eight locking holes 122 are positioned on the front panel for engaging drum holding mechanism 123 (FIG. 17). Holding mechanism 123 is positioned on mEADBP 154 approximately ⅔ of the distance forward from axle 115 in front of panel 119. It has a sliding bolt 124 which extends into locking holes 122. This locks drum 149 in place at each of eight sides of octagonal core 117. Drum 149 is rotated by hand crank 125 attached to pulley 116. Another pulley 126 is attached to traveling guide 147 (FIG. 14). Spring ,loaded idler pulley 127 is located between and below pulleys 116 and 126 (FIG. 15). Release handle 128 is attached to idler pulley 127 for releasing pulley belt 134 by rotating pulley upward and against the spring load.

Egg supply system (ESS) 13 (FIG. 18) has a funnel-shaped receptacle 137 with a narrow tube-shaped base. Attached to base is a length of tubing 138 (generally TYGON tubing). Egg supply 13 is attached to mEADBP 154 and is located above drum 149. Tube 138 is of sufficient length to reach the top side of the bolt of string 142 (FIG. 16) wrapped around drum 149. Located below drum 149 is rectangular-shaped pan 139 for catching any eggs that fall off of the bolt of string 142 as drum 149 is rotated (FIG. 12*b*). These eggs can then be recycled for attachment to string.

In operation, a spool of string 152 is placed on dowel 150. String is pulled from the spool, passed through string guide passed through the plates 146a (FIGS. 13a and 13b) of tensioner 146. The string is then fed through traveling guide 147 (FIG. 14) from the tensioner side and guide 155a to the drum side. After passing through string guide 155, the string is attached to the drum by forming a loop at the free end and slipping the loop over a screw 157 located on the inside of rear panel 118 (FIG. 16). The drum is then rotated by handcrank 125 in order to make a bolt of string 142 (FIG. 16) on drum 149 (FIGS. 12a and 12b). Once the drum has the desired number of lengths of string, it is stabilized by inserting bolt 124 into one of the locking holes 122 (FIG. 17). To prevent string from sliding on drum 149, lengths of tape 156 are placed across the bolt of string 142 at each of the eight twelve-inch intervals over each of rods 121 (FIG. 16). Next, the string is cut and the cut end is tied to a rod 121 or a front panel tab in order to maintain tension on the bolt of string 142. The pulley wheel assembly 148 is disconnected through spring-loaded pulley 27 in order to rotate drum 149 without movement of guide 147. Egg supply system (EES) 136 is loaded with beneficial insect eggs which can be eggs alone or eggs mixed with corn cob grits or any other suitable filler in order to regulate the number of eggs applied to the string. A small collecting tray 166 (FIG. 19) that fits under the bolt of string is inserted to collect eggs that fall through the bolt of cord upon each ⅛ rotation of drum 149. A narrow piece of wood 53 (FIGS. 20a and 20b), approximately equal to the width of the bolt of string 142 coated on one side with plastic sponge, is dipped into glue and applied across the bolt of string 142 in the center of the 12-inch interval. If more eggs per length of string is desired, then two or more bands of glue clan be equally spaced across the bolt of string. The egg supply tubing 138 (FIG. 18) is lifted down and eggs are distributed across the band(s) of glue. The collecting tray is removed and drum 149 is rotated to the next 12-inch interval by disengaging and then re-engaging bolt 124. This process is repeated until each of the eight 12-inch intervals contain a band(s) of eggs. At this point, a cut is made across the bolt of string by cutting lengthwise across one of the pieces of tape over one of rods. This enables removal of the entire bolt of string 142 in one eight-foot length. The bolt is laid lengthwise across a vertical board and a single length of string can be pulled off bolt and applied to plants. Alternately, the entire bolt can be packaged for overnight delivering by winding it around cardboard partitions. Finally, eggs that fell into the collecting tray (FIGS. 19a and 19b) and pan 139 are returned to the egg supply receptacle 137 for recycling.

The foregoing detailed description is for the purpose of illustration. Such detail is solely for that purpose and those skilled in the art can make variations therein without departing from the spirit and scope of the invention.

INDEX OF ELEMENTS DESIGNATED BY A NUMERAL

First Embodiment

10. Egg Attaching Device (EAD)
12. Glue Application System (GAS)
13. Wick Device
14. Egg Application System (EAS)
16. Locking Notch
17. EAD Housing (EADH)
18. EAD Base Plate (EADBP)
19. L-Shaped Bracket
20. String Delivery System (SDS)
21. Recirculating Hopper
22. String Supply Housing
23. Hopper Cover
23a. 45° Folds
24. Cylindrical Base Portion
25. Cover Opening
26. Funnel-Shaped Cover
27. Glue Container
28. Upwardly Extending Dowel
29. Reservoir Portion
30. Spool of String
31. String
32. Opening with Slots for Passage of String
33. Cover Portion of Glue Container
34. Funnel Opening
35. Air Vent
36. Fasteners
37. Air Vent Closing Screw
38. Inside Bottom of Base Portion
40. Housing Plate
41. Reservoir Holder
42. Fold-Over Retaining Bracket
43. Glue Delivery Assembly
44. String Tensioner Assembly
45. Tensioner
45a. Tensioner Plates
46. Drag Bar
47. Mounting Bracket
48. Drag Bar
50. String Guide
50a. String Guide Standoff
51. Pulley Wheel Assembly
52. Glue Pulley Wheel
53. V-Slot
54. Recirculating Hopper Pulley Wheel
55. V-Slot
56. Final Guide Pulley Wheel
57. T-Shaped Slot
60. Set Screw
61. Locking Wing Nuts
62. Pulley Wheel Axle Rod
63. Spur Gear Assembly
64. Spur Gear
65. Pulley Wheel V-Groove
66. Front-Half of Hopper
67. Egg Guide
68. Rear-Half of Hopper
69. Screw Mounting Hole
70. Screw Mounting Hole
71. EADH Front Panel
74. Viewing Window
75. Vertical Slot
76. Base Portion of Vertical Slot
78. Inner Upper Edge
79. Inner Vertical Side Walls
80. Inner Basal Walls
82. Cylindrical Cut-Out
83. Dowel
84. Funnel-Shaped Top
85. Air Supply Tube
86. Base of Funnel Shaped Top
88. Air Supply Line
89. Air Compressor
90. Sheet Metal Support
91. Recess
92. Recess 93. Egg-Lifting Device
94. Stopper
95. EADH Rear Panel
96. Modified Base of Glue Reservoir
97. Bung-Hole Fitting
98. Semi-Rigid Reinforced Tubing
99. Stopcock Valve
100. Rotating Union
101. Clean-Out Plug Screw
102. Outlet End
102a. Locking Nut
103. Galvanized Nipple
104. Galvanized Cap
105. Port
106. Copper Tube
107. Plastic Tubing
108. Elbow
109. Pinch Valve
110. U-Shaped Support
110a. Slot in Wick Device
110b. Bottom of U-Shaped Support
110c. Nap Side of Velcro
111. Copper Tubing
129. Flange Mount Bearings
130. End Bearings
131. Bolt and Bushing Fasteners
132. Wing Nut
133. Threaded Shaft
140. Filter
141. Retaining Screen
143. Needle Valve
144. Excess Air T-Outlet Alternate Embodiment 11. mEAD Egg Attaching Device
112. String Supply System (SSS)
113. Pulley Wheel - String Guide System (PWSGS)
114. Drum Winding System (DWS)
115. Axle
116. Pulley
117. Octagonal Shaped Core
118. Circular Shaped Rear Panel
119. Octagonal Shaped Front Panel
120. Tabs
121. Rods
122. Locking Holes
123. Drum Holding Mechanism
124. Sliding Bolt
125. Hand Crank
126. Pulley
127. Idler Pulley
128. Release Handle
134. Pulley Belt
136. Egg Supply System (ESS)
137. Funnel-Shaped Receptacle
138. Tubing
139. Pan
142. Bolt of String
143. String Tensioner
145. String Support
146. Tensioner System
146a. Tensioner Plates
147. Traveling String Guide Device
148. Pulley Wheel Assembly
149. Drum
150. Dowel
151. L-Shaped Bracket
152. Spool of String
154. Base Plate of mEAD (mEADBP)
155. String Guide
155a. String Guide
155b. String Guide
156. Length of Tape
157. Screw for String Attachment
158. Rotating Threaded Rod
159. Iron Support
159a. Screw Hole
160. Guide Rod
160a. Guide Rod Hole
161. Shaft Coupling
162. Pillow Block Sleeve Bearings
163. Angle Iron Frame
164a. Axle Rod
164b. Axle Rod
165. Frame Space Rod
166. Tray for Catching Overflow of Predator Eggs

We claim:

1. A device for attaching beneficial insect eggs to string comprising a string delivery means that includes a means for housing a spool of string, a spool of string, a means to guide said string from said housing means to a downstream portion of the device;

a pulley wheel assembly that includes a glue pulley wheel, a recirculating hopper pulley wheel, and a final guide pulley wheel;

a glue application system that includes a container means for holding a supply of glue, an arrangement of tubing between said container means and said glue pulley wheel, a means for controlling the flow of glue wherein said means is inserted in said tubing, and a means for contacting said string in the pulley wheel assembly with said glue wherein said means is a wick inserted in said glue pulley wheel and is connected to said container means by said tubing; and an egg supply system with recirculating hopper with an air lifting means for lifting eggs from the base of said hopper to glue coated string fed through the hopper by said pulley wheel assembly.

2. The device of claim 1 wherein said air lifting means for lifting eggs from the base of said hopper includes a device comprising a dowel having a longitudinally centered bored hole, a continuous airway, and a means for preventing eggs from falling into said tube which is attached to said funnel-shaped top at its base;

a length of tubing attached to said tube; and an air compressor connected to said length of tubing.

3. A device for attaching beneficial insect eggs to string comprising a string delivery means that includes a means for supporting a spool of string, a string tensioner means, a traveling string guide which allows string to be evenly spaced in a single layer on a drum for receiving said string, and a pulley wheel assembly;

a drum for receiving string in order to attach said insect eggs to each string; and an egg supply system for directing beneficial insect eggs to glue on said string that includes a container means for holding a supply of said eggs, and a length of tubing connected to said container means for applying eggs from said container means to glue on said string.

* * * * *